(12) United States Patent
Agorio et al.

(10) Patent No.: US 8,357,913 B2
(45) Date of Patent: Jan. 22, 2013

(54) METHOD AND APPARATUS FOR SAMPLE EXTRACTION AND HANDLING

(75) Inventors: Enrique Agorio, Lake Oswego, OR (US); James Edgar Hudson, Portland, OR (US); Michael Tanguay, Portland, OR (US); Jason Arjavac, Hillsboro, OR (US); Gerhard Daniel, Portland, OR (US)

(73) Assignee: FEI Company, Hillsboro, OR (US)

( * ) Notice: Subject to any disclaimer, the term of this patent is extended or adjusted under 35 U.S.C. 154(b) by 395 days.

(21) Appl. No.: 12/446,376

(22) PCT Filed: Oct. 20, 2007

(86) PCT No.: PCT/US2007/082030
§ 371 (c)(1),
(2), (4) Date: Oct. 14, 2009

(87) PCT Pub. No.: WO2008/051880
PCT Pub. Date: May 2, 2008

(65) Prior Publication Data
US 2010/0305747 A1  Dec. 2, 2010

Related U.S. Application Data

(60) Provisional application No. 60/927,719, filed on May 4, 2007, provisional application No. 60/853,183, filed on Oct. 20, 2006.

(51) Int. Cl.
*G01N 1/28* (2006.01)
*G21K 5/08* (2006.01)
(52) U.S. Cl. .................... 250/440.11; 250/311
(58) Field of Classification Search .. 250/440.11–443.1, 250/306–311
See application file for complete search history.

(56) References Cited

U.S. PATENT DOCUMENTS 5,254,438 A  10/1993  Owen et al.
5,270,552 A * 12/1993  Ohnishi et al. ................ 250/307
(Continued)

FOREIGN PATENT DOCUMENTS
EP  1204133  5/2002
(Continued)

OTHER PUBLICATIONS

Potter, Clinton S. et al., 'Robotic Grid Loading System for a Transmission Electron Microscope,'Journal of Structural Biology, 2004, pp. 431-440, vol. 146.

(Continued)

*Primary Examiner* — Robert Kim
*Assistant Examiner* — David E Smith
(74) *Attorney, Agent, or Firm* — Scheinberg & Associates, PC; Michael O. Scheinberg

(57) ABSTRACT

An improved method and apparatus for extracting and handling samples for STEM analysis. Preferred embodiments of the present invention make use of a micromanipulator and a hollow microprobe probe using vacuum pressure to adhere the microprobe tip to the sample. By applying a small vacuum pressure to the lamella through the microprobe tip, the lamella can be held more securely and its placement controlled more accurately than by using electrostatic force alone. By using a probe having a beveled tip and which can also be rotated around its long axis, the extracted sample can be placed down flat on a sample holder. This allows sample placement and orientation to be precisely controlled, thus greatly increasing predictability of analysis and throughput.

15 Claims, 18 Drawing Sheets

U.S. PATENT DOCUMENTS

| | | | |
|---|---|---|---|
| 5,315,123 | A | 5/1994 | Itoh et al. |
| 5,656,811 | A | 8/1997 | Itoh et al. |
| 5,847,821 | A | 12/1998 | Tracy et al. |
| 5,942,805 | A | 8/1999 | Winer et al. |
| 6,039,000 | A | 3/2000 | Libby et al. |
| 6,188,072 | B1 | 2/2001 | Chung |
| 6,300,628 | B1 | 10/2001 | Fujii et al. |
| 6,373,070 | B1 | 4/2002 | Rasmussen |
| 6,417,512 | B1 | 7/2002 | Suzuki |
| 6,420,722 | B2 | 7/2002 | Moore et al. |
| 6,497,194 | B1 | 12/2002 | Libby et al. |
| 6,521,890 | B2 | 2/2003 | Ishitani et al. |
| 6,527,967 | B1 * | 3/2003 | Suzuki .............. 216/62 |
| 6,538,254 | B1 | 3/2003 | Tomimatsu et al. |
| 6,570,170 | B2 | 5/2003 | Moore |
| 6,573,516 | B2 | 6/2003 | Kawakami |
| 6,576,900 | B2 | 6/2003 | Kelly et al. |
| 6,593,583 | B2 | 7/2003 | Iwasaki |
| 6,608,920 | B1 | 8/2003 | Su et al. |
| 6,681,039 | B1 | 1/2004 | Roberts et al. |
| 6,709,554 | B2 | 3/2004 | Ferranti et al. |
| 6,717,156 | B2 | 4/2004 | Sugaya et al. |
| 6,781,125 | B2 | 8/2004 | Tokuda et al. |
| 6,841,788 | B1 * | 1/2005 | Robinson et al. .......... 250/492.3 |
| 6,842,538 | B2 | 1/2005 | Lee et al. |
| 6,871,114 | B1 | 3/2005 | Green et al. |
| 6,927,391 | B2 | 8/2005 | Tokuda et al. |
| 6,963,068 | B2 | 11/2005 | Asselbergs et al. |
| 6,965,895 | B2 | 11/2005 | Smith et al. |
| 6,982,429 | B2 | 1/2006 | Robinson et al. |
| 6,993,177 | B1 | 1/2006 | Bachelder |
| 7,002,152 | B2 | 2/2006 | Grunewald |
| 7,005,636 | B2 | 2/2006 | Tappel |
| 7,034,316 | B2 | 4/2006 | Wagner et al. |
| 7,041,985 | B1 * | 5/2006 | Wang et al. .............. 250/442.11 |
| 7,045,275 | B2 | 5/2006 | Lee et al. |
| 7,047,099 | B2 | 5/2006 | Shanmugasundram et al. |
| 7,069,101 | B1 | 6/2006 | Arackaparambil et al. |
| 7,095,024 | B2 | 8/2006 | Adachi et al. |
| 7,103,439 | B1 | 9/2006 | Bode et al. |
| 7,205,554 | B2 | 4/2007 | Tokuda et al. |
| 7,205,560 | B2 * | 4/2007 | Tokuda et al. ............. 250/492.3 |
| 7,297,965 | B2 | 11/2007 | Kidron et al. |
| 7,348,556 | B2 | 3/2008 | Chitturi et al. |
| 7,381,971 | B2 | 6/2008 | Moore et al. |
| 7,408,178 | B2 | 8/2008 | Tappel |
| 7,414,252 | B2 | 8/2008 | Moore et al. |
| 7,423,263 | B2 * | 9/2008 | Hong et al. ................... 250/304 |
| 7,442,924 | B2 | 10/2008 | Giannuzzi et al. |
| 7,465,945 | B2 | 12/2008 | Tokuda et al. |
| 7,470,918 | B2 | 12/2008 | Tokuda et al. |
| 7,511,282 | B2 | 3/2009 | Agorio et al. |
| 7,550,750 | B2 | 6/2009 | Tokuda et al. |
| 7,615,745 | B2 | 11/2009 | Schampers et al. |
| 7,700,367 | B2 | 4/2010 | Fujii |
| 7,842,920 | B2 | 11/2010 | Lundquist |
| 7,880,151 | B2 | 2/2011 | Wells |
| 7,888,639 | B2 | 2/2011 | Tokuda et al. |
| 2002/0079463 | A1 | 6/2002 | Shichi et al. |
| 2003/0183776 | A1 * | 10/2003 | Tomimatsu et al. ..... 250/442.11 |
| 2005/0010317 | A1 | 1/2005 | Hadar et al. |
| 2006/0011868 | A1 | 1/2006 | Kidron et al. |
| 2006/0017016 | A1 | 1/2006 | Tappel |
| 2006/0102608 | A1 * | 5/2006 | Katsuta et al. ........... 219/121.83 |
| 2006/0186336 | A1 | 8/2006 | Giannuzzi et al. |
| 2006/0284357 | A1 * | 12/2006 | Goko et al. ..................... 269/21 |
| 2007/0272854 | A1 * | 11/2007 | Agorio et al. ................. 250/304 |

FOREIGN PATENT DOCUMENTS

| | | |
|---|---|---|
| JP | 60136315 | 7/1985 |
| JP | 62174918 | 7/1987 |
| JP | 5052721 | 3/1993 |
| JP | 6342750 | 12/1994 |
| JP | 08005528 | 1/1996 |
| JP | 09306411 | 11/1997 |
| JP | 11108810 | 4/1999 |
| JP | 11183339 | 7/1999 |
| JP | 11-265679 | 9/1999 |
| JP | 11330186 | 11/1999 |
| JP | 2000155081 | 6/2000 |
| JP | 2000241319 | 9/2000 |
| JP | 2000268768 | 9/2000 |
| JP | 2001319954 | 11/2001 |
| JP | 2002141382 | 5/2002 |
| JP | 2002148159 | 5/2002 |
| JP | 2003203959 | 7/2003 |
| JP | 2004111097 | 4/2004 |
| JP | 2004164966 | 6/2004 |
| JP | 2006144825 | 6/2006 |
| JP | 2008008850 | 1/2008 |
| WO | 2002075806 | 9/2002 |
| WO | 2008049133 | 4/2008 |
| WO | 2008049134 | 4/2008 |
| WO | 2008051880 | 5/2008 |
| WO | 2008051937 | 5/2008 |

OTHER PUBLICATIONS

Giannuzzi, Lucille A., et al., 'FIB Lift-Out for Defect Analysis,' Microelectronic Failure Analysis: Desk Reference, Nov. 2002, pp. 29-35.

Giannuzzi, Lucille A., et al., 'FIB Lift-Out Specimen Preparation Techniques,' Introduction to Focused Ion Beams, 2005, Chapter 10.

Langford, Richard M., 'Focused Ion Beams Techniques for Nanomaterials Characterization,' Microscopy Research and Technique, 2006, pp. 538-549, vol. 69.

Lee, Jon C., et al., 'The Versatile Application for In-Situ Lift-Out TEM Sample Preparation by Micromanipulator and Nanomotor,' 2005.

Lensing, Kevin, et al, 'Integrated Metrology and Wafer-Level Control,' Jun. 1, 2006, 6 pgs.

Japanese Office Action for Japanese Application No. 2009-533583, Jul. 5, 2012, 3 pgs.

Japanese Office Action for Japanese Application No. 2009-533599, Jun. 6, 2012, 5 pgs.

Japanese Office Action for Japanese Application No. 2009-533597, Jun. 27, 2012, 3 pgs.

Japanese Office Action for Japanese Application No. 2009-533596, Jun. 27, 2012, 4 pgs.

* cited by examiner

METHOD AND APPARATUS FOR SAMPLE EXTRACTION AND HANDLING

The present application claims priority from PCT Application No. PCT/US2007/082030, filed Oct. 20, 2007, and U.S. Prov. Pat. App. No. 60/853,183, filed Oct. 20, 2006, and U.S. Prov. Pat. Appl. No. 60/927,719, filed on May 4, 2007, all of which are hereby incorporated by reference.

TECHNICAL FIELD OF THE INVENTION

The present invention relates to the extraction and handling of samples for transmission electron microscopes and scanning transmission electron microscopes.

BACKGROUND OF THE INVENTION

Semiconductor manufacturing, such as the fabrication of integrated circuits, typically entails the use of photolithography. A semiconductor substrate on which circuits are being formed, usually a silicon wafer, is coated with a material, such as a photoresist, that changes solubility when exposed to radiation. A lithography tool, such as a mask or reticle, positioned between the radiation source and the semiconductor substrate casts a shadow to control which areas of the substrate are exposed to the radiation. After the exposure, the photoresist is removed from either the exposed or the unexposed areas, leaving a patterned layer of photoresist on the wafer that protects parts of the wafer during a subsequent etching or diffusion process.

The photolithography process allows multiple integrated circuit devices or electromechanical devices, often referred to as "chips," to be formed on each wafer. The wafer is then cut up into individual dies, each including a single integrated circuit device or electromechanical device. Ultimately, these dies are subjected to additional operations and packaged into individual integrated circuit chips or electromechanical devices.

During the manufacturing process, variations in exposure and focus require that the patterns developed by lithographic processes be continually monitored or measured to determine if the dimensions of the patterns are within acceptable ranges. The importance of such monitoring, often referred to as process control, increases considerably as pattern sizes become smaller, especially as minimum feature sizes approach the limits of resolution available by the lithographic process. In order to achieve ever-higher device density, smaller and smaller feature sizes are required. This may include the width and spacing of interconnecting lines, spacing and diameter of contact holes, and the surface geometry such as corners and edges of various features. Features on the wafer are three-dimensional structures and a complete characterization must describe not just a surface dimension, such as the top width of a line or trench, but a complete three-dimensional profile of the feature. Process engineers must be able to accurately measure the critical dimensions (CD) of such surface features to fine tune the fabrication process and assure a desired device geometry is obtained.

Typically, CD measurements are made using instruments such as a scanning electron microscope (SEM). In a scanning electron microscope (SEM), a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface. As features continue to get smaller and smaller, however, there comes a point where the features to be measured are too small for the resolution provided by an ordinary SEM.

Transmission electron microscopes (TEMs) allow observers to see extremely small features, on the order of nanometers. In contrast SEMs, which only image the surface of a material, TEM also allows analysis of the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite site. Samples, also referred to as lamellae, are typically less than 100 nm thick.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface.

Because a sample must be very thin for viewing with transmission electron microscopy (whether TEM or STEM), preparation of the sample can be delicate, time-consuming work. The term "TEM" as used herein refers to a TEM or an STEM and references to preparing a sample for a TEM are to be understood to also include preparing a sample for viewing on an STEM. The term "S/TEM" as used herein also refers to both TEM and STEM.

Several techniques are known for preparing TEM specimens. These techniques may involve cleaving, chemical polishing, mechanical polishing, or broad beam low energy ion milling, or combining one or more of the above. The disadvantage to these techniques is that they are not site-specific and often require that the starting material be sectioned into smaller and smaller pieces, thereby destroying much of the original sample.

Other techniques generally referred to as "lift-out" techniques use focused ion beams to cut the sample from a substrate or bulk sample without destroying or damaging surrounding parts of the substrate. Such techniques are useful in analyzing the results of processes used in the fabrication of integrated circuits, as well as materials general to the physical or biological sciences. These techniques can be used to analyze samples in any orientation (e.g., either in cross-section or in plan view). Some techniques extract a sample sufficiently thin for use directly in a TEM; other techniques extract a "chunk" or large sample that requires additional thinning before observation. In addition, these "lift-out" specimens may also be directly analyzed by other analytical tools, other than TEM. Techniques where the sample is extracted from the substrate within the FIB system vacuum chamber are commonly referred to as "in-situ" techniques; sample removal outside the vacuum chamber (as when the entire wafer is transferred to another tool for sample removal) are call "ex-situ" techniques.

Samples which are sufficiently thinned prior to extraction are often transferred to and mounted on a metallic grid covered with a thin electron transparent film for viewing. FIG. 1A shows a sample mounted onto a prior art TEM grid 10. A typical TEM grid 10 is made of copper, nickel, or gold. Although dimensions can vary, a typical grid might have, for example, a diameter of 3.05 mm and have a middle portion 12 consisting of cells 14 of size 90×90 $\mu m^2$ and bars 13 with a width of 35 μm. The electrons in an impinging electron beam will be able to pass through the cells 14, but will be blocked by the bars 13. The middle portion 12 is surrounded by an edge portion 16. The width of the edge portion is 0.225 mm. The edge portion 16 has no cells, with the exception of the orientation mark 18. The thickness 15 of the thin electron transparent support film is uniform across the entire sample carrier, with a value of approximately 20 nm. TEM specimens to be analyzed are placed or mounted within cells 14.

For example, in one commonly used ex-situ sample preparation technique, a protective layer 22 of a material such as tungsten is deposited over the area of interest on a sample surface 21 as shown in FIG. 2 using electron beam or ion beam deposition. Next, as shown in FIGS. 3-4, a focused ion beam using a high beam current with a correspondingly large beam size is used to mill large amounts of material away from the front and back portion of the region of interest. The remaining material between the two milled rectangles 24 and 25 forming a thin vertical sample section 20 that includes an area of interest. The trench 25 milled on the back side of the region of interest is smaller than the front trench 24. The smaller back trench is primarily to save time, but the smaller trench also prevents the finished sample from falling over flat into larger milled trenches which may make it difficult to remove the specimen during the micromanipulation operation.

As shown in FIG. 5, once the specimen reaches the desired thickness, the stage is tilted and a U-shaped cut 26 is made at an angle partially along the perimeter of the sample section 20, leaving the sample hanging by tabs 28 at either side at the top of the sample. The small tabs 28 allow the least amount of material to be milled free after the sample is completely FIB polished, reducing the possibility of redeposition artifacts accumulating on the thin specimen. The sample section is then further thinned using progressively finer beam sizes. Finally, the tabs 28 are cut to completely free the thinned lamella 27. Once the final tabs of material are cut free lamella 27 may be observed to move or fall over slightly in the trench. A completed and separated lamella 27 is shown in FIG. 6.

The wafer containing the completed lamella 27 is then removed from the FIB and placed under an optical microscope equipped with a micromanipulator. A probe attached to the micromanipulator is positioned over the lamella and carefully lowered to contact it. Electrostatic forces will attract lamella 27 to the probe tip 29 as shown in FIG. 7. The tip 29 with attached lamella is then typically moved to a TEM grid 10 as shown in FIG. 8 and lowered until lamella is placed on the grid in one of the cells 14 between bars 13.

Samples which require additional thinning before observation are typically mounted directly to a TEM sample holder. FIG. 1B shows a typical TEM sample holder 31, which comprises a partly circular 3 mm ring. In some applications, a sample 30 is attached to a finger 32 of the TEM sample holder by ion beam deposition or an adhesive. The sample extends from the finger 32 so that in a TEM (not shown) an electron beam will have a free path through the sample 31 to a detector under the sample. The TEM sample is typically mounted horizontally onto a sample holder in the TEM with the plane of the TEM sample perpendicular to the electron beam, and the sample is observed.

A common in-situ extraction technique is described in U.S. Pat. No. 6,570,170 to Moore, which describes extracting out a sample by making a "U"-shaped cut and then cutting the sample at an angle from the missing side of the "U" to undercut and free the sample. After the sample is freed, a probe is attached to the sample by FIB (42)-induced chemical vapor deposition and it is lifted out. This process typically results in a chunk-type sample, which is generally wedge shaped and approximately 10×5×5 μm in size. This sequence of steps is illustrated in FIG. 9 to FIG. 10.

The chunk is then transported by the attached microprobe to a TEM sample holder and attached directly to the sample holder as shown in FIG. 11 (again with FIB-induced CVD). The end of the sample with the attached probe is then cut free as shown in FIG. 12. At this point, the TEM sample holder with the attached sample is typically transferred to another FIB system where the sample is thinned into an electron-transparent thin section. The sample can then be imaged with an electron beam in a TEM or STEM.

Unfortunately, preparation of TEM samples using such prior art methods of sample extraction suffer from a number of shortcomings. Such methods are typically very time-consuming and labor intensive. CD metrology often requires multiple samples from different locations on a wafer to sufficiently characterize and qualify a specific process. In some circumstances, for example, it will be desirable to analyze from 15 to 50 TEM samples from a given wafer. When so many samples must be extracted and measured, using known methods the total time to process the samples from one wafer can be days or even weeks. Even though the information that can be discovered by TEM analysis can be very valuable, the entire process of creating and measuring TEM samples has historically been so labor intensive and time consuming that it has not been practical to use this type of analysis for manufacturing process control.

Specifically, the ex-situ method discussed above is not very reliable and requires a great deal of operator experience. Even with experienced operators, the success range is only about 90%. It can be time consuming and difficult to locate a lamella site and the extraction probe must be very carefully moved into position to avoid damaging the sample or the probe tip. Once a lamella has been completely freed, it can move in unpredictable ways; it can fall over in the trench or in some cases it can actually be pushed up and out of the trench by electrostatic forces. This movement can make it difficult to locate and/or pick up the lamella with the extraction probe. The electrostatic attraction between the probe and the sample is also somewhat unpredictable. In some cases, the lamella may not stay on the probe tip. Instead, it can jump to a different part of the probe. In other cases, the lamella may fall off while the sample is being moved. If the lamella is successfully transferred to the TEM grid, it can be difficult to get the lamella to adhere to the grid support film rather than the probe tip. The lamella will often cling to the probe tip and must be essentially wiped off onto the film. As a result, it is virtually impossible to control the precise placement or orientation of the lamella when it is transferred to the TEM grid.

The in-situ method described above is more predictable and reliable; however it is considerably more time-consuming. A significant amount of time is taken up by the steps of attaching the microprobe to the sample, attaching the sample to the sample holder, and cutting the microprobe free. The sample is also moved to and attached to the TEM grid inside the FIB instrument, which requires more valuable FIB time.

Speeding up the process of sample extraction and transfer would provide significant advantages in both time and potential revenue by allowing a semiconductor wafer to be more rapidly returned to the production line. Full or partial automation of the process of sample removal and transport would not only speed up the process, but it would also reduce the level of expertise required of operators and technicians thus lowering personnel costs.

What is needed is an improved method for TEM sample analysis, including sample creation, extraction, and measurement.

SUMMARY OF THE INVENTION

An object of the invention, therefore, is to provide an improved method for TEM sample analysis. Preferred embodiments of the present invention provide improved methods for partially or fully automating TEM sample extraction and handling in order to make the process of creating and analyzing TEM samples less labor intensive and to increase throughput of TEM analysis.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Preferred embodiments of the present invention provide a fully or partially automated process for TEM sample extraction and handling. Increased throughput and a less labor-intensive process will allow S/TEM based metrology to be better utilized in a wafer fabrication facility to provide rapid feedback to process engineers to troubleshoot or improve processes.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable.

Figure 1A:
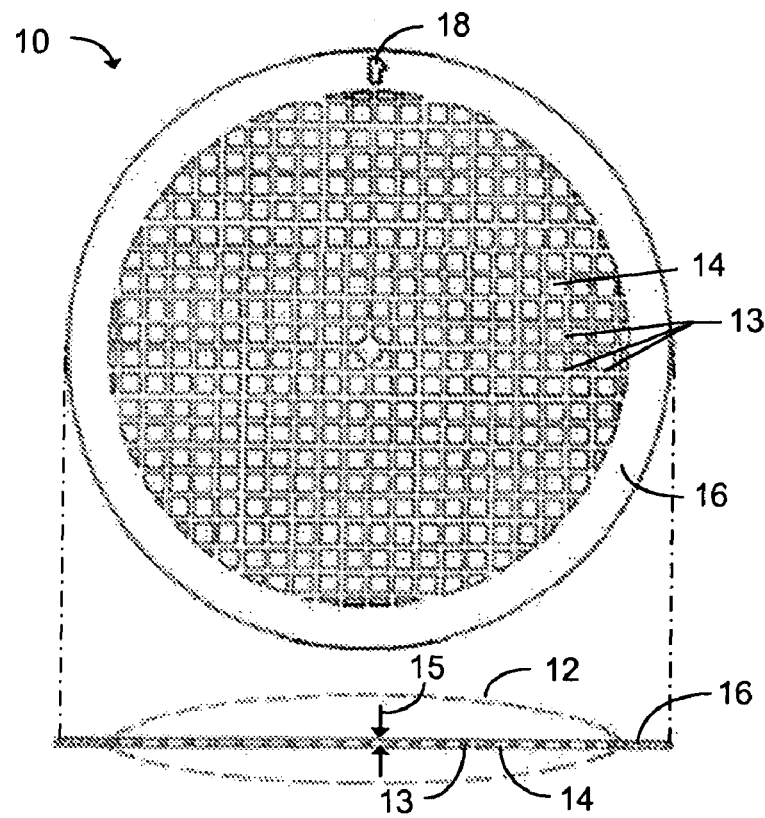
FIG. 1A shows a typical prior art TEM grid.
Figure 1B:
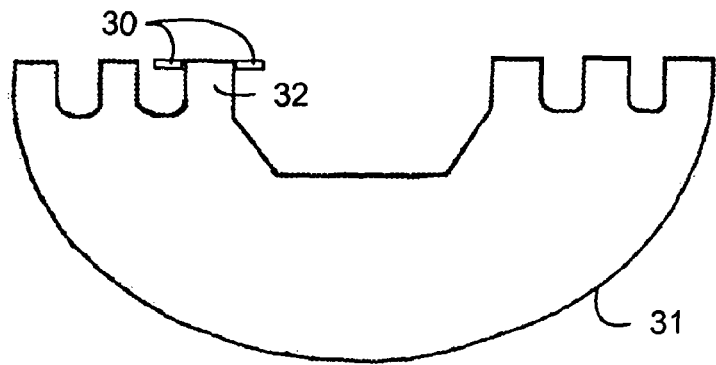
FIG. 1B shows a typical prior art TEM sample holder.
Figure 2:
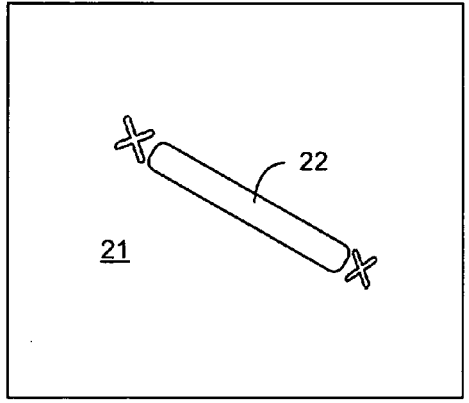
FIGS. 2-5 illustrate the steps in an ex-situ sample preparation technique according to the prior art.
Figure 3:
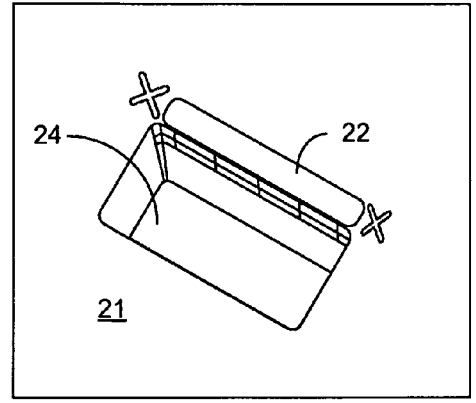
Figure 4:
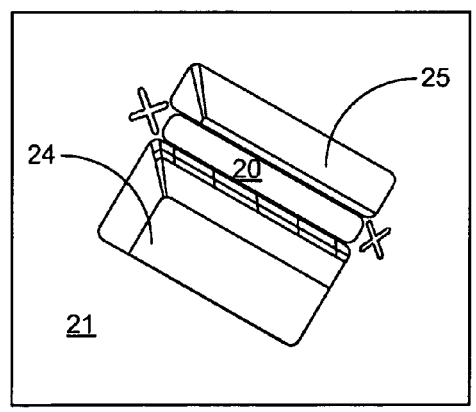
Figure 5:
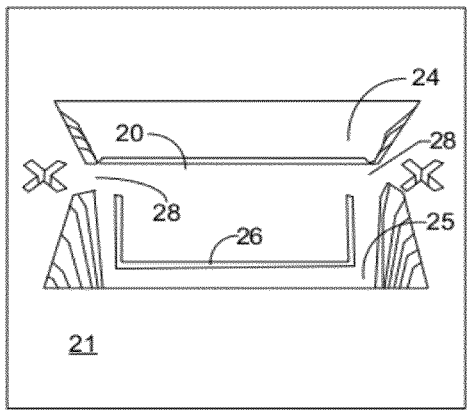
Figure 6:
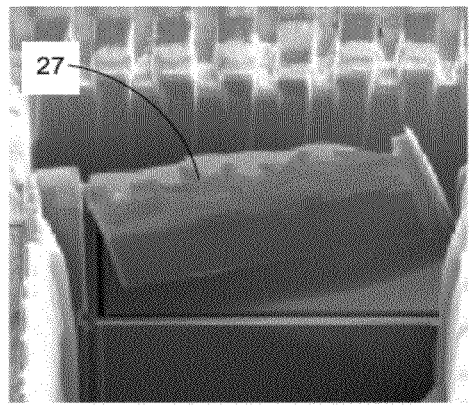
FIG. 6 is a micrograph of a completed and separated lamella according to the prior art.
Figure 7:
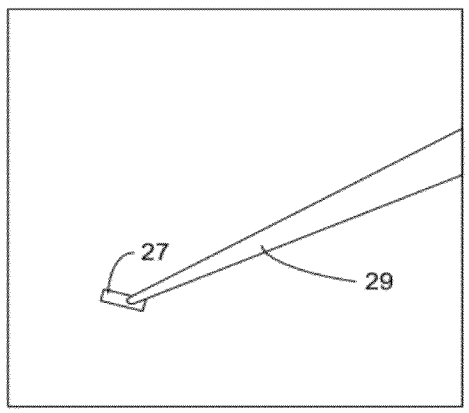
FIGS. 7-8 illustrate the transfer of a lamella using a probe and electrostatic attraction according to the prior art.
Figure 8:
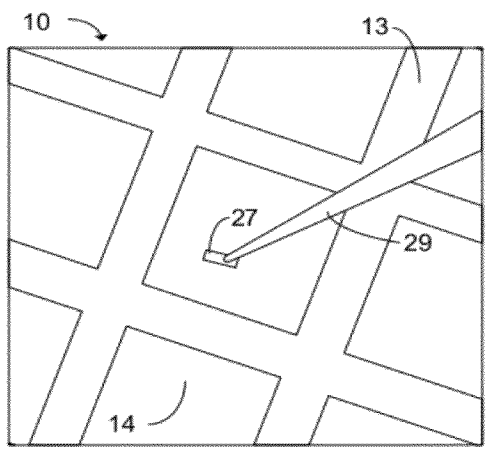
Figure 13:
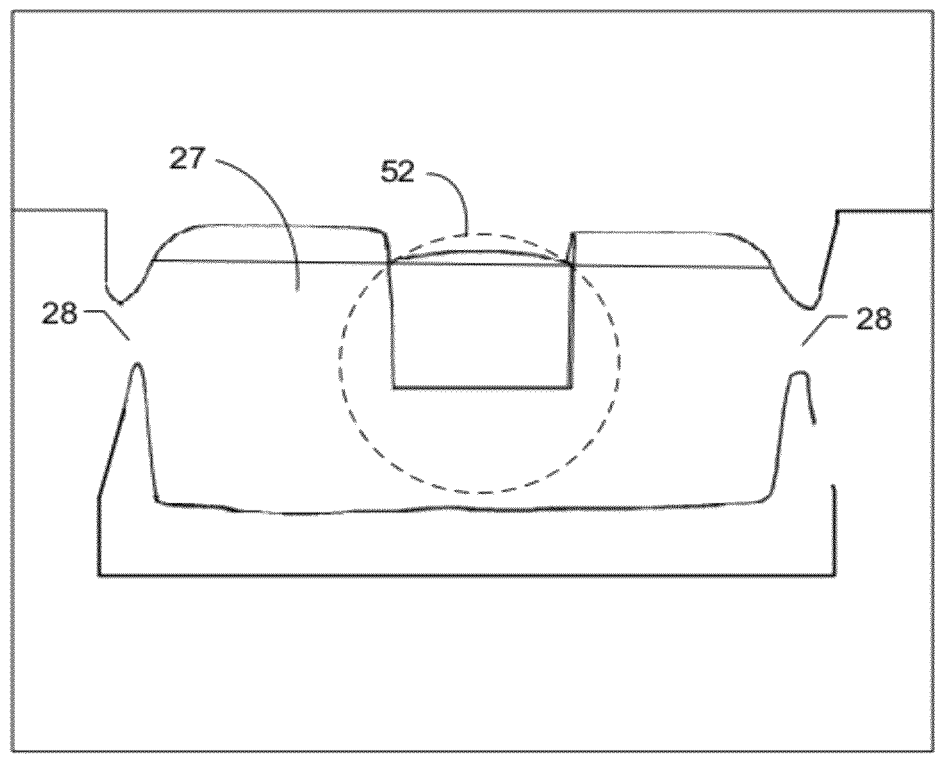
FIG. 13 shows a thinned lamella sample suitable for extraction according to the present invention.

In a preferred embodiment of the present invention, one or more lamellae are first created on a wafer or other substrate. Preferably, a number of lamellae can be created using an automated ex-situ process where a lamella is thinned in place before removal as described in U.S. Provisional App. 60/853, 183 by Blackwood et al. for "Method for S/TEM Sample Analysis" (which is hereby incorporated by reference). The sample milling process discussed above with reference to FIGS. 4 to 8 can be used to create one or more lamellae at different sites on a wafer or other substrate. Preferably, the lamellae are not completely separated from the substrate as shown in FIG. 6. Instead, as shown in FIG. 13, each lamella is only partially separated leaving a small tab 28 of material at least at one end holding the lamella 27 in place. This helps prevent the lamella from falling over in the milled cavities on either side of the lamella (which can make it much more difficult to locate and extract the lamella using a probe).

Once the desired lamellae have been created, the entire wafer can be transferred to a separate fully or partially automated ex-situ extraction tool, described herein. Wafers are preferably transferred to the sample extraction tool by way of a multi-wafer carrier and auto-loading robot, as in well known in the art, although wafers can also be transferred manually. The list of all lamella sites, including the x-y coordinates for each lamella location, for each wafer can be transferred to the extraction tool from the FIB system used to mill the lamellae. The sample extraction tool then uses a mechanical stage to navigate to each lamella site. The lamellae are extracted using an electrostatic/pressure manipulator and placed onto a TEM grid. The lamella extraction process is preferably fully automated. Alternatively, the extraction process can be completely or partially controlled manually.

Figure 14:
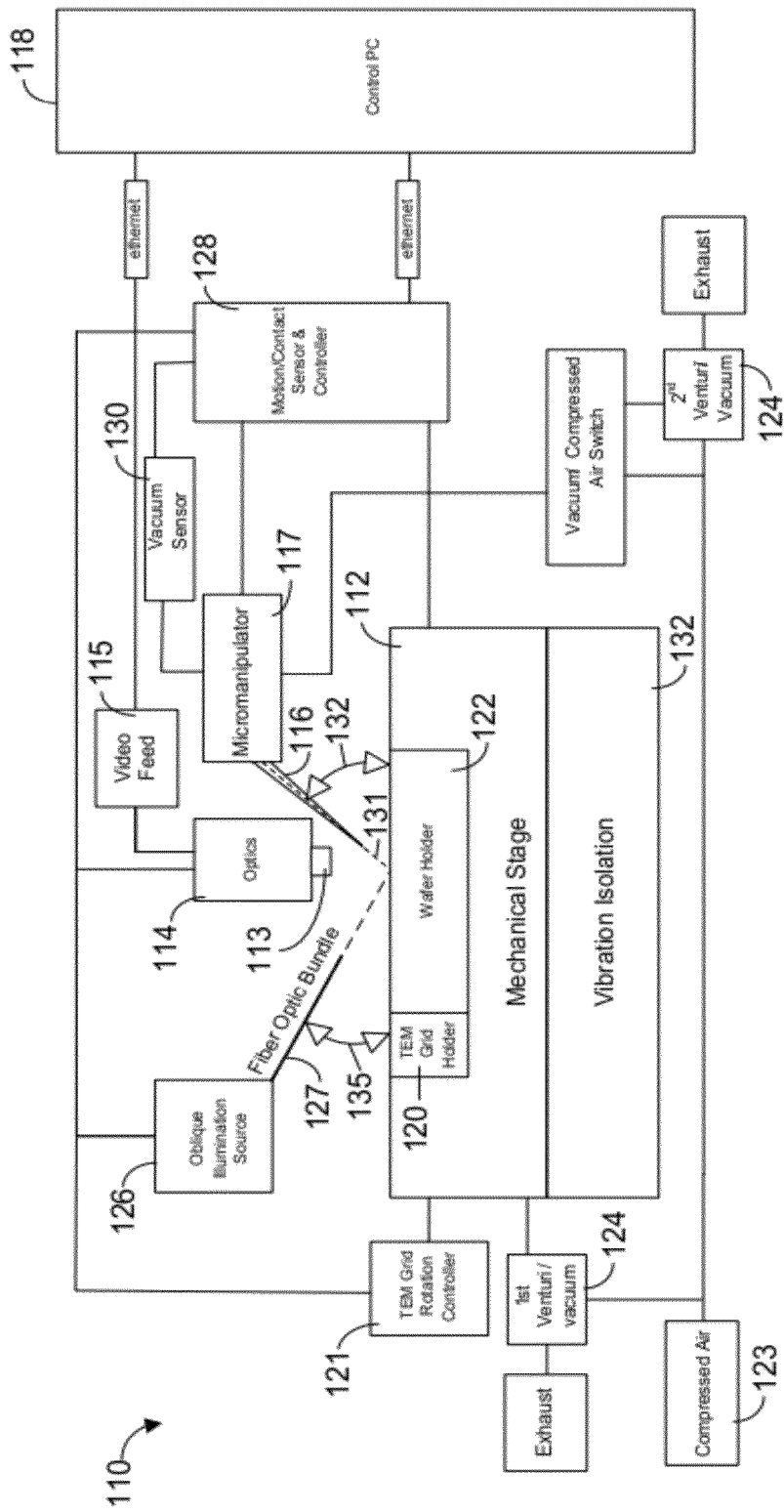
FIG. 14 shows an ex-situ sample extraction device according to the present invention.

FIG. 14 is a block diagram showing a preferred embodiment of ex-situ sample extraction tool 110 (hereinafter "Ex-Situ Plucker" or "ESP") according to the present invention. In a preferred embodiment, the ESP is a standalone tool for ex-situ extraction of samples. The ESP comprises a TEM specimen extractor having a mechanical stage 112, an optical microscope 114 with a video feed 115, and a probe 116 (also referred to herein as a microprobe) for extracting the samples.

Figure 18:
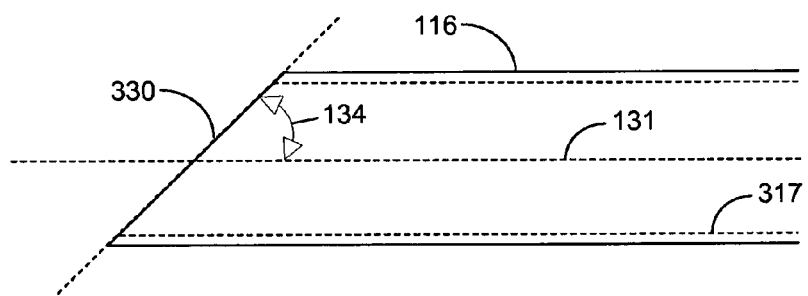
FIG. 18 shows a beveled probe according to the present invention.

Referring also to FIG. 18, probe 116 preferably comprises a cylindrical hollow tube with a flat tip beveled at approximately 45 degrees through which a vacuum can be applied in order to draw the sample to the probe tip. Probe 116 is oriented so that the cylindrical (longitudinal) axis of the probe is at an approximately 45 degree angle relative to the wafer (substrate) upper surface. Where the sample to be extracted has a vertical sample face, this results in the probe being also oriented at a 45 degree angle relative to the sample face. Probe 116 preferably comprises a pulled 1 mm borosilicate tube with a face beveled at 45 degrees. Suitable probes can be manufactured, for example, by using standard borosilicate micropipettes with the tips modified by using a micropipette puller such as a Narishige PC-10 to create long, thin microcapillaries with an outer diameter of 10 to 12 µm.

In one preferred embodiment, the ESP comprises the following components that are integrated and controlled via a single control point (e.g. a Control PC) 118: a wafer holder 122 mounted on an XYZR mechanical substrate stage 112, a micromanipulator system 117 including a probe holder and motors and an XYZ probe stage that can rotate a microprobe about cylindrical (longitudinal) axis of a probe, a rotatable TEM grid holder 120, a TEM grid rotation controller 121, an optional separate grid stage (not shown) (both the wafer holder and the TEM grid holder can be mounted on one mechanical stage), a pulled micromachined micropipette probe 116 with 45 degree flat tip (possibly roughened to minimize adhesion), an optional controlled environment to minimize effects of humidity and temperature (not shown), one or more vacuum pumps 124 or other devices for applying vacuum through the probe 116, an air pressure source 123 such as a source of compressed air, an optical microscope 114 with lens 113 to image the substrate, a light optical system 126 (using a fiber optic bundle 127) used to illuminate the substrate from an oblique angle (135) to facilitate imaging and/or machine-based pattern recognition, a motion/contact sensor and controller 128, an air flow or vacuum sensor 130, and a vibration isolation table 132.

In the preferred embodiment of FIG. 14, the ESP is operably connected to (or integrated with) a computer station 118, which uses software for implementing sample extraction and manipulation. Computer station 118, through appropriate software, can receive the x-y coordinates for the sample to be extracted from the FIB system used to create the lamella. The location of each lamella can then be matched with a corresponding TEM grid location once the samples are extracted and transferred to the TEM grid (typically one lamella per cell). This allows for data traceability through the entire process so that the final TEM results can be automatically matched back to the particular sample site on the original wafer. Computer station 118 is also preferably operably connected to the stage controllers and micromanipulator controllers to position the sample and grid stages and to position the microprobe.

By applying a small vacuum pressure to the lamella through the microprobe tip, the lamella can be controlled much more accurately than by using electrostatic force alone as in the prior art. The lamella is held securely in place and is not as easily dropped as in the prior art. Minimizing the electrostatic attraction between the probe tip and the sample (as discussed in greater detail below) makes it much more likely that the sample will stay precisely where it is placed rather than continuing to adhere to the probe tip. Even where electrostatic attraction is used to adhere the sample to the probe tip (in whole or in conjunction with vacuum pressure) the angled bevel on the microprobe, along with the ability to rotate the probe tip 180 degrees around its long axis, allows the lamella to be placed down flat on the TEM grid film, which tends to maximize the attraction between the sample and the TEM grid film causing the sample to adhere to the film and stay at the position where it is placed. This allows sample placement and orientation to be precisely controlled, thus greatly increasing predictability of analysis and throughput (because the TEM stage does not need to be adjusted as often between samples).

Figure 15:
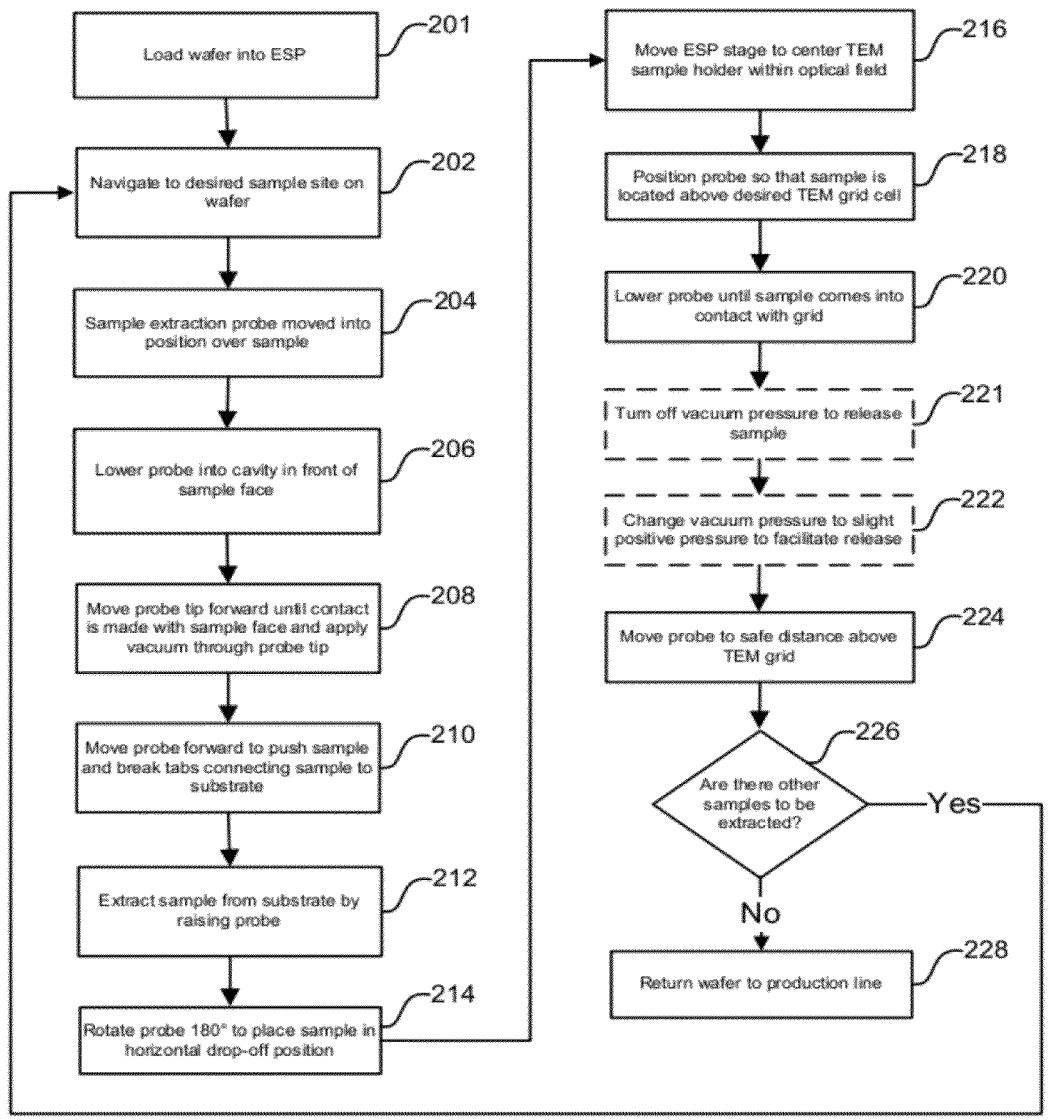
FIG. 15 is a flowchart showing the steps in extracting a sample using an ex-situ sample extraction device according to the present invention.

FIG. 15 is a flowchart showing the steps in extracting multiple samples from a wafer according to the present invention. These steps are preferably carried out and controlled automatically by computer station 118 via computer readable instructions, although the steps can also be completely or partially controlled manually.

In step 201, a wafer containing milled but unextracted samples is loaded into the ESP wafer holder 122. In a preferred embodiment, the samples have been created as discussed above in reference to FIGS. 4 to 8 except that the lamellae are preferably only partially separated from the substrate leaving a small tab of material at either end holding the lamella in place. The wafer holder 122 is mounted on an XYZR mechanical substrate stage. The wafer can be aligned automatically or manually using known methods.

Figure 19A:
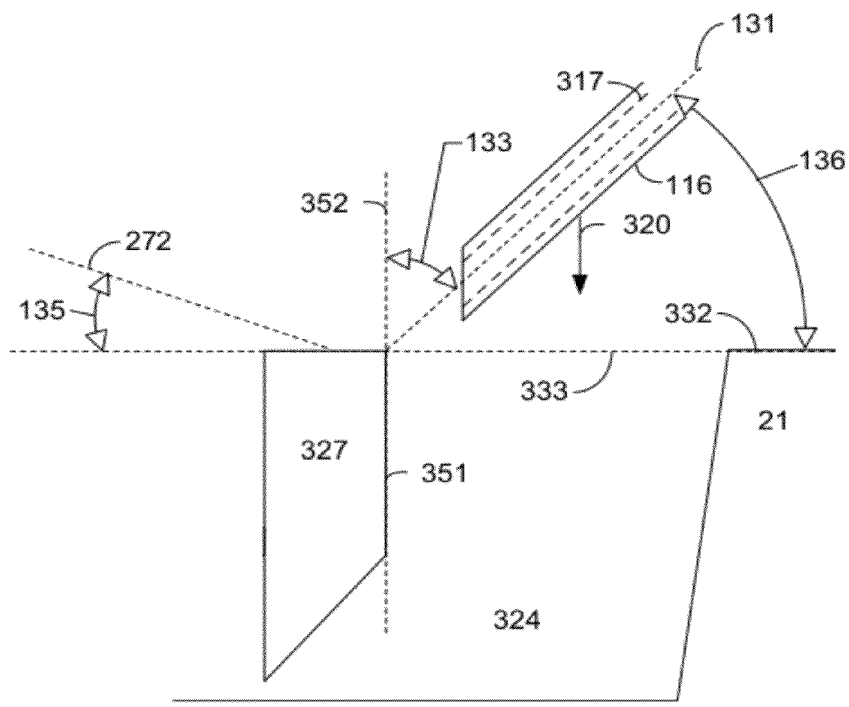
FIGS. 19A-19B illustrate lowering a probe tip into contact with a sample to be extracted according to the present invention.
Figure 19B:
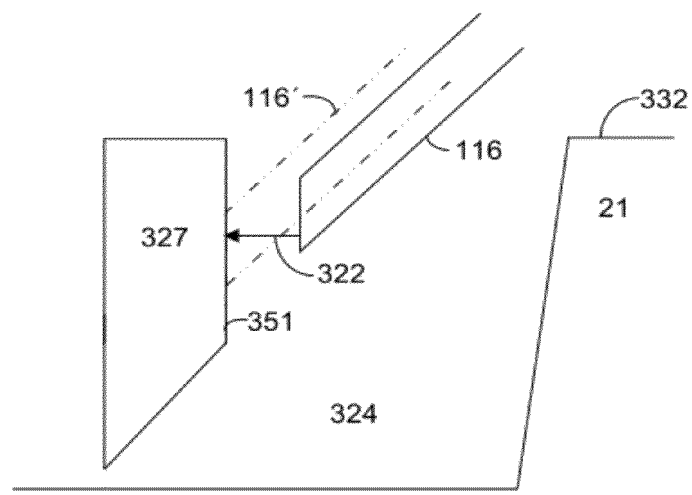
Figure 20:
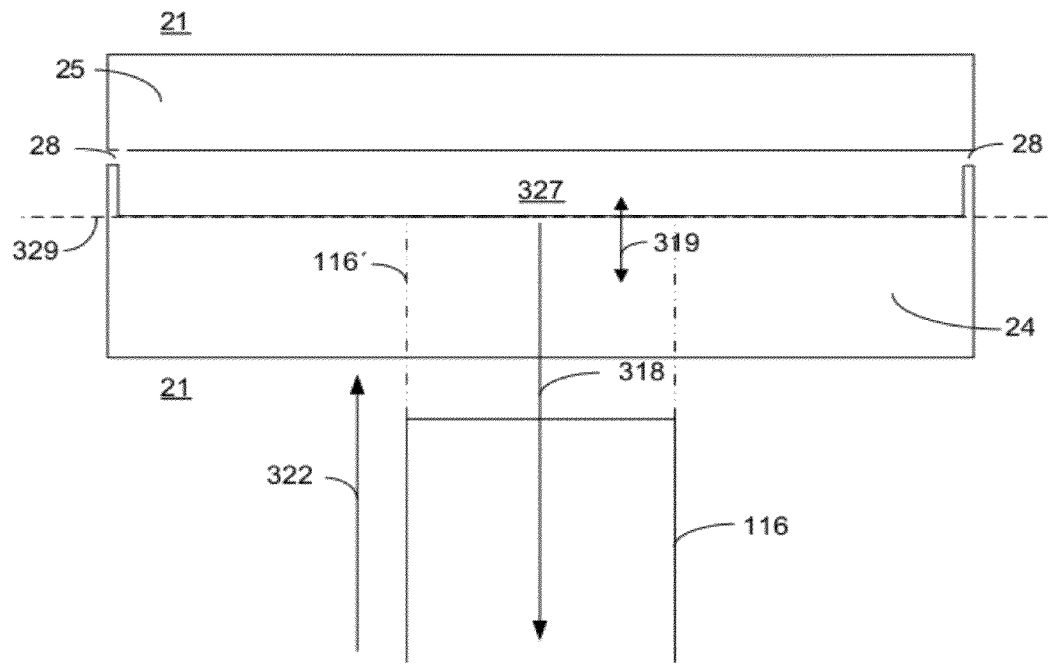
FIGS. 20-21 illustrate moving a probe tip into contact with a sample to be extracted according to the present invention.
Figure 21:
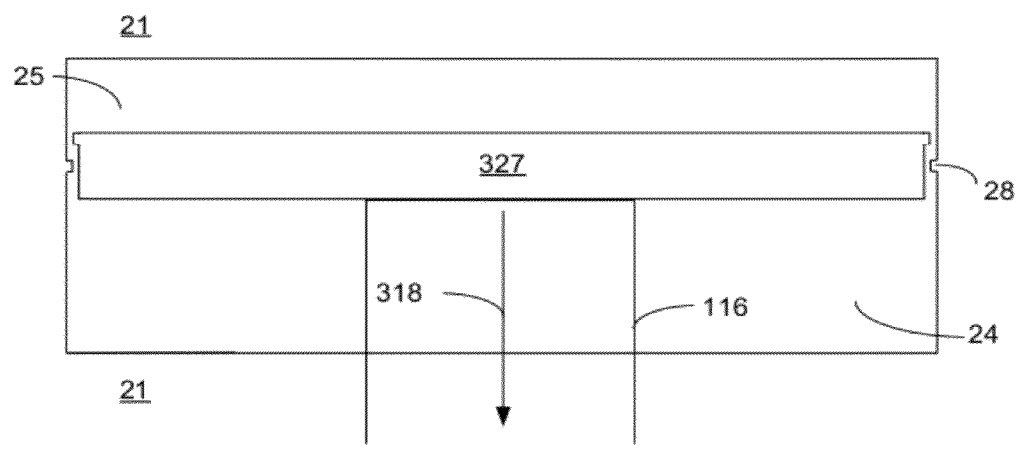

After the wafer substrate is aligned, in step 202, the ESP can navigate to a sample site using positional data imported from the FIB system used to create the samples. The ESP optical microscope 114 is used to image the substrate at the sample site. The exact sample location and orientation is determined and the probe is moved into position. Referring also to FIGS. 20-21, the sample stage is rotated so that the orientation of the probe is generally perpendicular to the lamella face (although as shown in FIGS. 14 and 19A-B the probe will typically be tilted down so that the intersection of the cylindrical axis of the probe 131 with the plane of the substrate surface forms an acute angle 136). In other words, the cylindrical axis of the probe lies in a plane which is perpendicular to the sample face. This process can be performed by an operator viewing the sample site by using manual controls to move the probe and/or the substrate to position the probe tip in the milled cavity behind the sample. In a preferred embodiment, this process can be performed automatically using machine-based image recognition.

Both oblique and bright field illumination should be used to facilitate sample location and grid alignment. The oblique illumination should be used to image the lamella cavity to locate the lamella to be extracted. Referring also to FIGS. 14, 19A, and 20, assuming that the lamella itself lies in the X-Y plane 329, the light 272 will preferably be directed in a plane perpendicular to the X-Y plane of the lamella 327 and at an acute angle 135 relative to the substrate surface so that light reflecting off of the surface of the substrate 332 will not enter the acceptance angle of the lens 113 of the optical microscope 114. More preferably, the light will be directed at an angle of approximately 20 degrees relative to the substrate surface.

Figure 16:
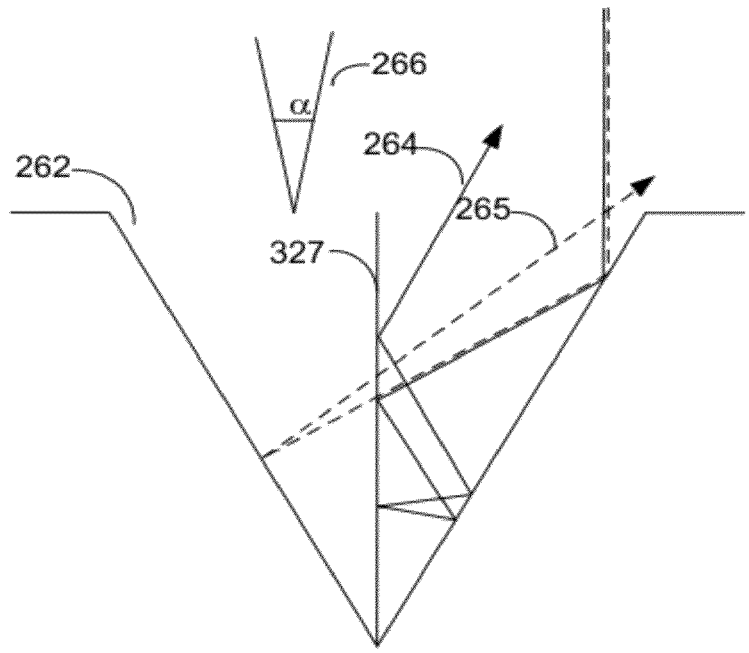
FIG. 16 is an example of a ray diagram showing the possible path of a beam of light when using top down illumination.
Figure 17:
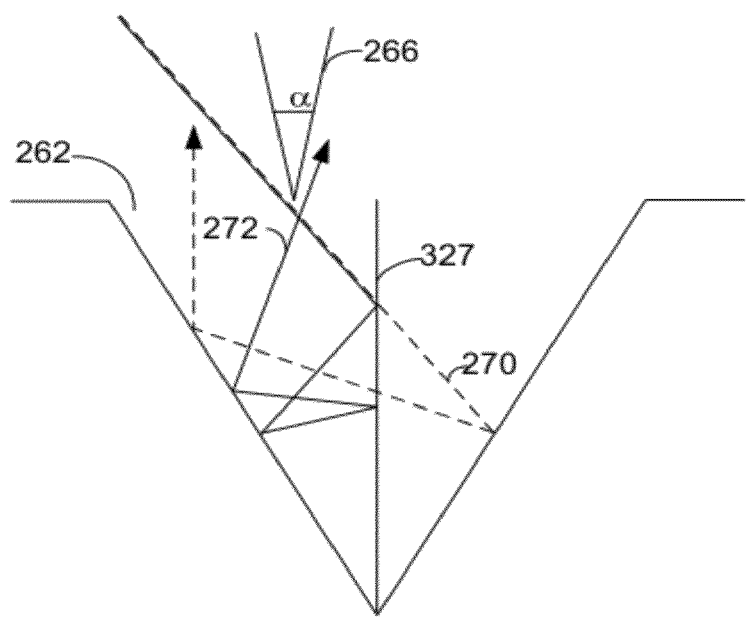
FIG. 17 is an example of a ray diagram showing the possible path of a beam of light when using oblique illumination.

Due to the angled walls of the lamella cavity, very poor image contrast is achieved within the cavity with top down illumination, since very little light enters the acceptance angle of the lens. As shown in FIGS. 16 and 17, due to the multiple reflections that will occur within the cavity, the amount of signal will be highly dependent on the wall angles within the cavity, these may vary significantly from one application to another. As a result, in some circumstances the illumination may need to be directed at an angle other than the 90 degree angle described above. In a preferred embodiment, the illumination angle should be adjustable, either manually by an operator or automatically. Bright field illumination can be used to allow imaging of alignment marks and TEM grids.

Unfortunately, sometimes a lamella may be missing from a cavity or positioned improperly. It that event, it is important to be able to quickly determine whether the lamella is present. In FIG. 16, dashed line 265 represents top-down illumination with no lamella present. As shown in FIG. 16, with top down illumination into the lamella cavity 262 and no lamella present, the light rays 264 will undergo multiple reflections and will not reenter the acceptance angle 266 of the lens (not shown). Likewise, with lamella 327 present in the cavity 262, light rays (shown by solid line 264) will also reflect at an angle outside acceptance angle 266. Thus, with top down illumination, the entire lamella cavity 262 will appear dark (whether or not a lamella 327 is present).

With oblique illumination, however, more reflected light enters the lens. As shown in FIG. 17, dashed line 270 represents oblique illumination with no lamella present. In that case, light rays will reflect off the two cavity sidewalls and enter the lens. Thus, the left half of the cavity 262 will appear brighter when the lamella is absent. Line 272 represents oblique illumination with the lamella 327 in place. In that case, reflected light will tend to escape the lens and the cavity 262 will appear dark (although the top of the lamella 327 itself may be visible.) Thus, with oblique illumination it can be readily determined whether a lamella is still within the cavity and whether it is at approximately the expected position. Depending upon the slope of the cavity walls and of the lamella face, the proper illumination angle may be adjusted with respect to the wafer plane and with respect to an axis perpendicular to the wafer to optimize sample location.

The oblique illumination can be supplied, for example, by way of a fiber optic bundle mounted at an appropriate oblique angle relative to the substrate surface. Preferably, the illumination source will be mounted opposite the probe and micromanipulator so that the sample to be extracted can be positioned with the illumination coming from one side and the probe from the other. It is also preferable that the illumination source be mounted in the same plane as the probe. As a result, rotating the sample stage so that the lamella face is perpendicular to the probe will also positions the sample properly relative to the illumination source.

In step 204, the sample extraction probe is moved into position over the sample to be extracted. As shown in FIG. 19A, in order to extract the sample, the ESP probe tip 330 is oriented so that it is roughly perpendicular to the desired probe attachment site, typically in the center of the sample as shown in FIGS. 20-21. As shown in FIGS. 18-19B, the ESP probe tip 330 is also preferably beveled at an angle 134 of approximately 45 degrees, and the entire ESP probe 116 is oriented at an angle 136 of approximately 45 degree relative to the wafer upper surface (shown by dashed line 333). Where the sample to be extracted has a vertical sample face, this results in the angle 133 of probe 116 relative to the sample face (shown by dashed line 352) also being a 45 degree angle. As a result, the beveled probe face is substantially parallel to the sample face. The internal walls of the probe are indicated by dashed lines 317.

To extract the sample, in step 206, the ESP probe is lowered into the cavity in front of the sample face, such as the rectangular area 324 adjacent to one of the sample faces 351 as shown in FIG. 19A. The arrow 320 in FIG. 19A indicates the direction of movement as the probe is lowered into position.

While the probe tip should be as large as possible so that the vacuum will provide a stronger pull on the lamella, it must also be small enough to fit into the cavity in front of the sample face to a sufficient depth for the probe face to contact the side of the sample so that the sample can be drawn to the probe tip. A suitable probe contact on a sample structure according to the present invention is shown by the dashed circle 52 in FIG. 13.

Persons of ordinary skill in the art will recognize that the internal diameter of the probe will greatly affect air flow through the tube when a vacuum is applied. A larger internal diameter will allow for a more powerful vacuum. However, the internal diameter will desirably be smaller than the smallest dimension of the sample to be extracted to prevent the sample from being pulled into the probe interior. In a preferred embodiment, the probe tip has a roughened face to minimize surface contact between the sample and the probe and thus minimize any electrostatic or other attraction between the sample and the probe as discussed below.

Referring also to FIGS. 20-21, in step 208, the probe 116 is then moved toward the sample face 351 (to the position shown by dashed line 116") and a vacuum applied through the open probe tip. The arrow 322 in FIG. 20 indicates the direction of movement as the probe 116 is moved forward to make contact with the sample. Arrow 318 shows the direction of air flow when the vacuum is applied. In step 210, once the probe tip makes contact with the sample face 351, the probe 116 can be pushed slightly forward to break any remaining connection between the sample and the substrate. It may be necessary to dither the probe back and forth as shown by arrow 319 in order to completely separate the sample.

The sample is held against the probe tip by a combination of electrostatic force and the vacuum pressure exerted through the probe tip. In some embodiments, the probe can be held in place by electrostatic forces alone. When vacuum pressure is used to hold the sample in place, the probe tip will preferably be adapted to minimize the electrostatic attraction between the sample and probe tip. For example, the probe tip can have a roughened face to minimize surface contact between the sample and the probe or it can be coated with a material that reduces the electrostatic attraction. Minimizing the electrostatic attraction makes it easier to release the sample and to more precisely place the sample at a desired location.

Also, in some embodiment, a probe having a conductive coating can be used to facilitate a contact sensor to determine when the probe tip is in contact with the sample. Sample contact may also be determined by using a flow sensor to monitor pressure changes in the vacuum applied through the probe tip.

Figure 22:
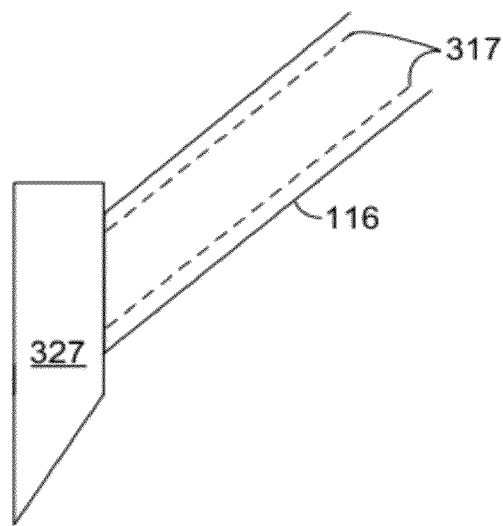
FIGS. 22-25 illustrate steps in the transfer of an extracted sample to a TEM grid according to the present invention.
Figure 23:
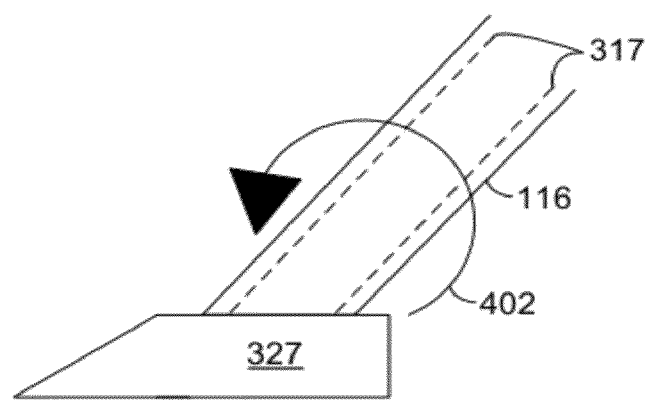

In step 212, the sample can then be lifted away from the wafer until it is safely above the substrate. As shown in FIGS. 22-23, in step 214, the probe is then rotated 180 degrees, as shown by arrow 402, to place the sample in a horizontal drop-off position. After rotation, the sample face will lie in a plane parallel to the substrate surface. As discussed above, the ESP probe tip 330 is preferably beveled at an angle of approximately 45 degrees, and the entire ESP probe is oriented at an approximately 45 degree angle to the sample face. This allows the beveled probe tip to be substantially parallel to the vertical sample face for sample extraction and also be substantially parallel to the horizontal support film after rotation. Skilled persons will recognize that the angle of the bevel and the angle of the entire probe can be varied. However, the sum of the two angles should typically be approximately 90 degrees where the sample has a substantially vertical face. For example, if a 60 degree bevel is used, the probe should be oriented at an angle of approximately 30 degrees (with respect to the sample face). Where angles other than 45 degrees are used, the TEM grid may have to be tilted to allow the sample to be placed flat on the TEM grid after the probe is rotated. In another preferred embodiment, the sample holder, such as a TEM grid, could be mounted vertically. In that case, rotation would not be necessary and the sample (held vertically by the probe tip) could be placed directly on the sample holder.

Figure 24:
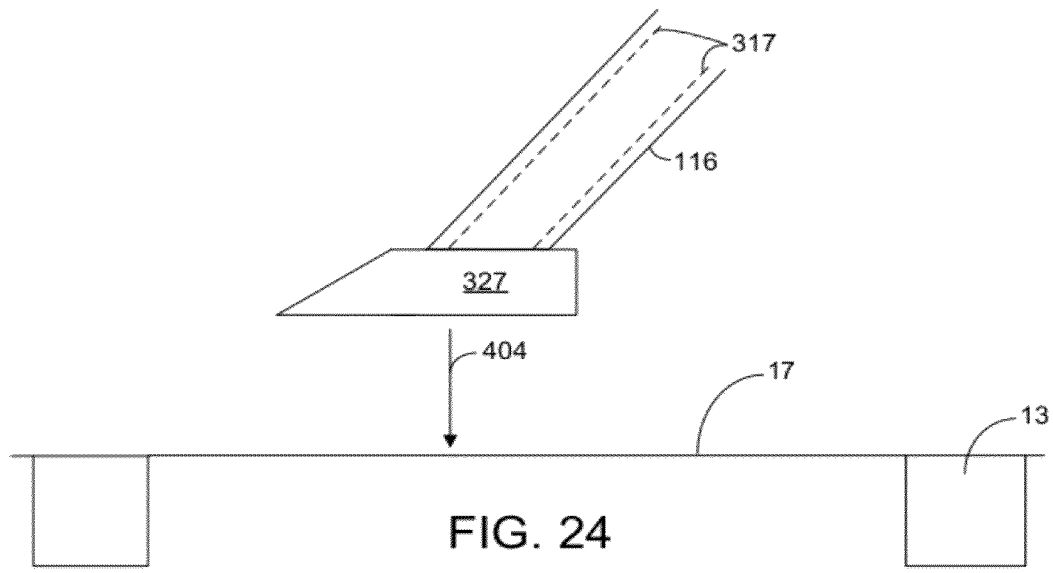
Figure 25:
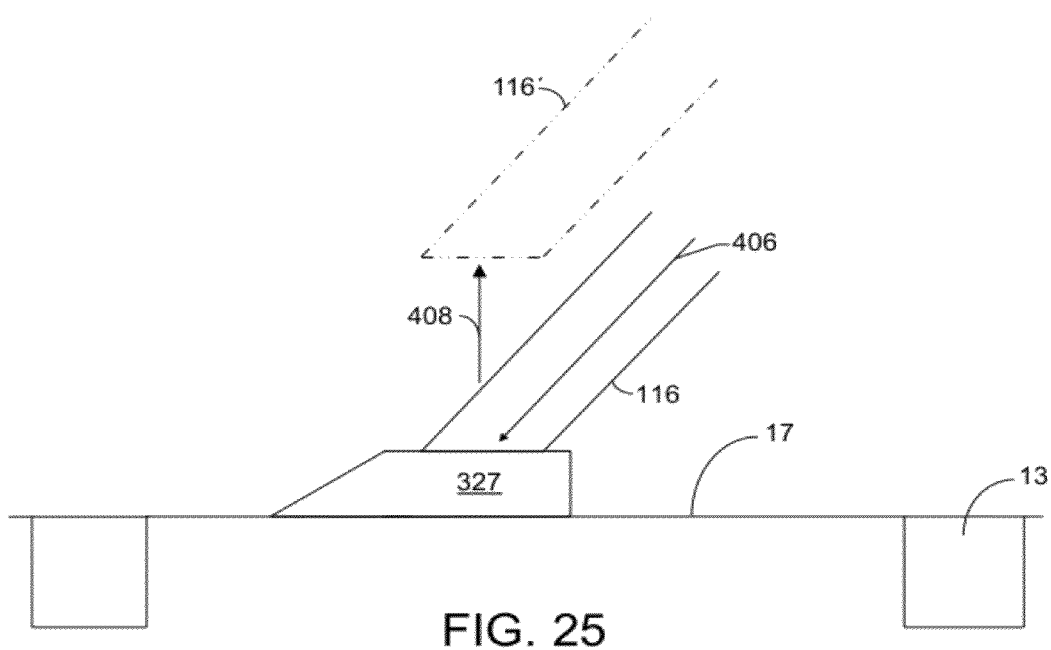

In step 216, the ESP stage is then moved so that the TEM grid holder is centered in the microscope optical field. The TEM grid holder is preferably mounted on a rotating stage so that the grid can be aligned to the XY axis of the wafer stage by rotating the TEM grid. Preferably, the stage can also be tilted if a non-45 degree bevel/probe orientation is used. The grid can also be rotated in the appropriate direction to account for orientation errors in the positioning of the sample. In step 218, the probe is positioned so that the sample is located above the desired TEM grid cell. In step 220, the probe 116 is lowered until the sample 327 comes into contact with the grid support film 17 as shown in FIGS. 24-25. Line 404 indicates the direction of movement of the probe 116 as the sample 327 is placed onto the support film 17. Contact can be determined by an appropriate contact sensor or controlled automatically based on known positions and calibration data. The particular film used for the TEM grid is preferably a film having a smooth and uniform surface. A firmer surface is better for ensuring good surface contact between the lamella and the film to facilitate the transfer and accurate placement of the lamella.

Once the sample is placed onto the TEM grid surface, in many cases the lamella will adhere to the film surface even if the vacuum through the probe tip remains turned on. In step 221, the vacuum pressure is optionally turned off to facilitate the release of the sample from the probe tip. In some embodiments, in optional step 222, the vacuum pressure can be changed to a slight over-pressure 406 in order to force the release of a sample that remains adhered to the probe tip.

The probe is then moved to a safe distance above the TEM grid in step 224 as shown in FIG. 25. Line 408 indicates the direction of movement of the probe after the sample has been released. If there are other samples to be extracted (step 226), the process described in steps 202-224 is repeated. Once all samples have been extracted, the wafer can be returned to the production line (step 228).

The present invention provides a number of significant advantages over the prior art. Using typical methods for TEM sample preparation, it takes highly trained and experienced operators approximately 3 hours to create and extract one sample lamella suitable for TEM analysis. For current in-line metrology techniques like top-down SEM or CD-SEM analysis, as many as 20 different sites across a wafer might be need to be measured. Using prior art methods of TEM sample preparation, it would take about 60 hours just to prepare suitable TEM samples from 20 different sites. The extraction and transfer takes up a large portion of the time required to create and extract a TEM sample. Using the present invention, however, results in a significant improvement in the TEM sample preparation process. The present invention can greatly reduce the time required to extract and transfer samples to the STEM for analysis. The use of the present invention, along with the improved sample creation methods described in U.S. Provisional App. 60/853,183 by Blackwood et al. for "Method for S/TEM Sample Analysis" (which is hereby incorporated by reference) reduces the time required to sample 20 different sites on a wafer surface to about 6 hours.

Also, because so much of the TEM sample preparation must be performed manually, the process is very labor intensive and requires the use of highly skilled operators (which of course translates into high labor costs). The increased throughput and reproducibility of the TEM analysis provided by the present invention will allow TEM based metrology on objects such as integrated circuits on semiconductor wafer to be used for in-line process control. For example, TEM analysis according to the present invention could be utilized in a wafer fabrication facility to provide rapid feedback to process engineers to troubleshoot or improve processes. This kind of process control for the very small features that can only be measured by TEM is not possible using prior art TEM sample preparation methods.

Preferred embodiments of the present invention also provide a modified sample structure that will allow the sample extraction tool discussed above to be used with "chunk-type" samples, such as those typically used by in-situ techniques. As discussed above with reference to FIGS. 10-21, one common in-situ extraction technique involves extracting a wedge-shaped sample from a substrate by attaching a probe tip to the sample using FIB deposition and transferring the sample to a TEM sample holder for further thinning.

One integrated instrument suite designed for this type of in-situ extraction of chunk samples for TEM analysis is the Ultraview™ system available from FEI Company, the assignee of the present invention. Aspects of the Ultraview™ systems are described in U.S. Pat. No. 6,963,068 to Asselbergs et al. for "Method for the manufacture and transmissive irradiation of a sample, and particle-optical system," which is hereby incorporated by reference. The Ultraview™ system integrates an in-line dual beam (SEM/FIB) system (for example, the FEI Expida™ series) for sample extraction, a lab based small chamber dual beam system (for example, the FEI Strata™ series) for sample thinning and SEM/STEM imaging, and a TEM (for example, the FEI Tecnai™ series) for atomic resolution imaging. A sealed transfer capsule to transport the TEM grid from one instrument to another without breaking chamber vacuum. The grid is placed in a sealed transfer capsule that can be extracted from the in-line dual beam system. The capsule and samples can then be transported to the lab for further processing while the wafer continues in the manufacturing process. The sample is then transferred in the lab to a small-chamber dual beam system, where it is milled to final thickness, before STEM or TEM imaging.

A preferred embodiment of the present invention makes use of a modified sample structure having one or more vertical "wings" that provide a suitable surface face for extraction using the ESP tool described above. This modified sample structure is also compatible with existing automated sample handling systems such as the FEI Ultraview™ system. Rather than extracting the samples in-situ (as is customary for chunk-type samples), once the desired samples have been milled using a FIB system, the substrate is preferably transferred to the ESP where the samples are extracted and loaded onto a TEM sample holder.

Figure 26:
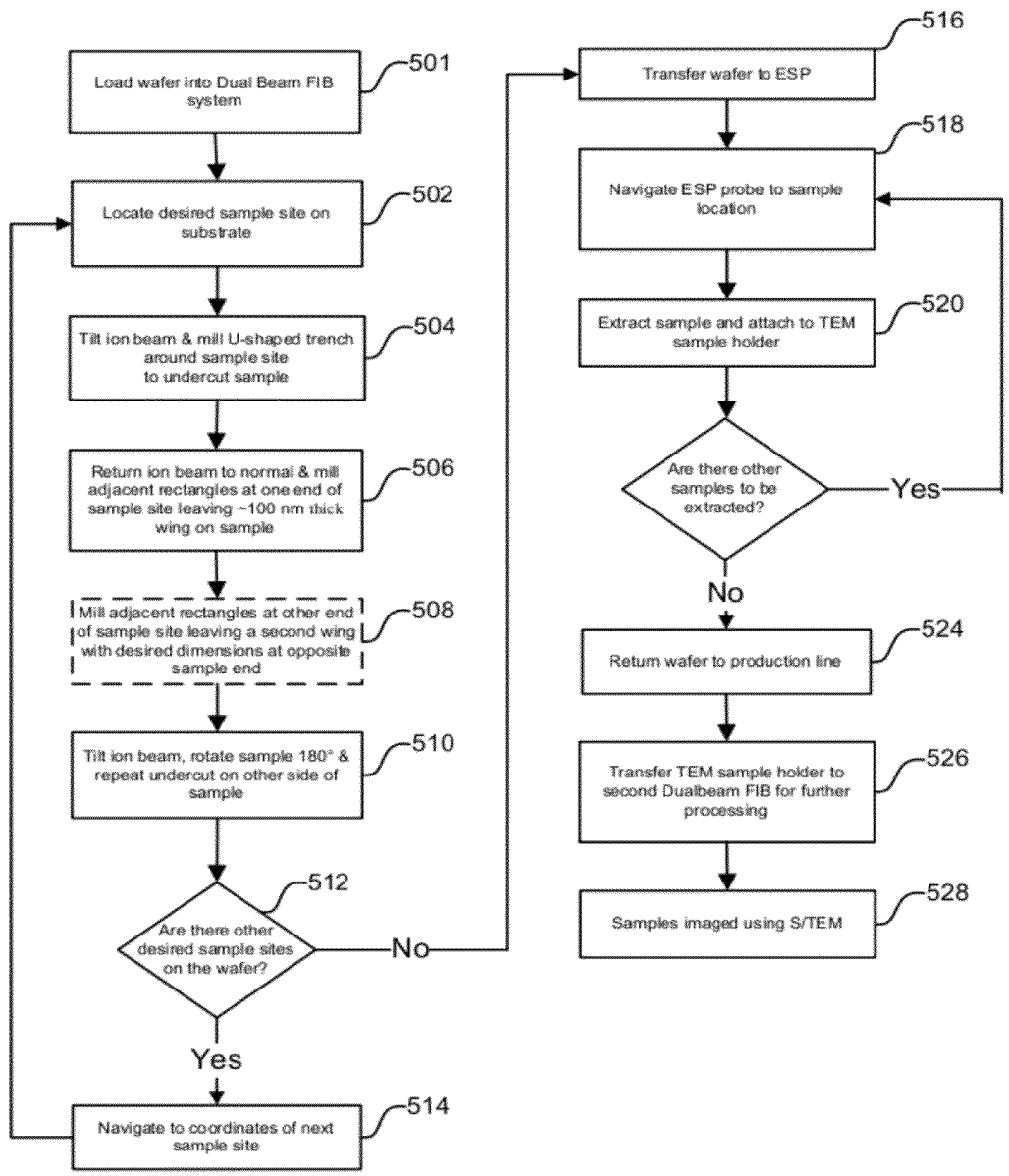
FIG. 26 is a flowchart showing the steps in creating and extracting a modified chunk-type sample according to the present invention.

FIG. 26 is a flowchart showing the steps of creating one or more samples according to a preferred embodiment of the present invention. First, in step 501, a substrate such as a semiconductor wafer is loaded into a Dual Beam FIB system. Wafers are preferably transferred by way of a multi-wafer carrier and auto-loading robot, as in well known in the art, although wafers can also be transferred manually.

In step 502, the location of a sample (containing a feature of interest) to be extracted from a substrate 640 is determined. For example, the substrate may be a semiconductor wafer or portion thereof and the portion to be extracted may include a portion of an integrated circuit that is to be observed using a TEM. One or more fiducial marks 644 may be milled into the substrate in order to help orient the ion beam and locate the precise location of the sample to be extracted.

Once the desired sample has been located, in step 504, an ion beam 646 is used to mill a U-shaped trench surrounding the desired sample section 652 (and containing the feature of interest). This trench will preferably be somewhat wider than trenches used in the prior art to allow for the creation of the sample "wings" discussed below. Preferably, the FIB will be tilted with respect to the sample surface (45 degrees for example) so that the trench at least partially undercuts the sample.

In step 506, FIB milling is used to form a thin sample section or wing 650 at one end of the chunk-type center section 652, preferably approximately 5-10 μm away from the position of the feature of interest (although the sample milling can be closer to the feature of interest when the precise position of the feature is known). The vertical face of wing 650 can be used to extract the sample using the ESP sample extraction tool as discussed above. In step 508, an optional second wing can be formed on the other end of the center sample section and ultimately used to secure the sample onto a TEM sample holder, as also discussed below. The larger size of wedge-shaped center section 652 helps insure that the feature of interest is included in the sample.

Figure 27:
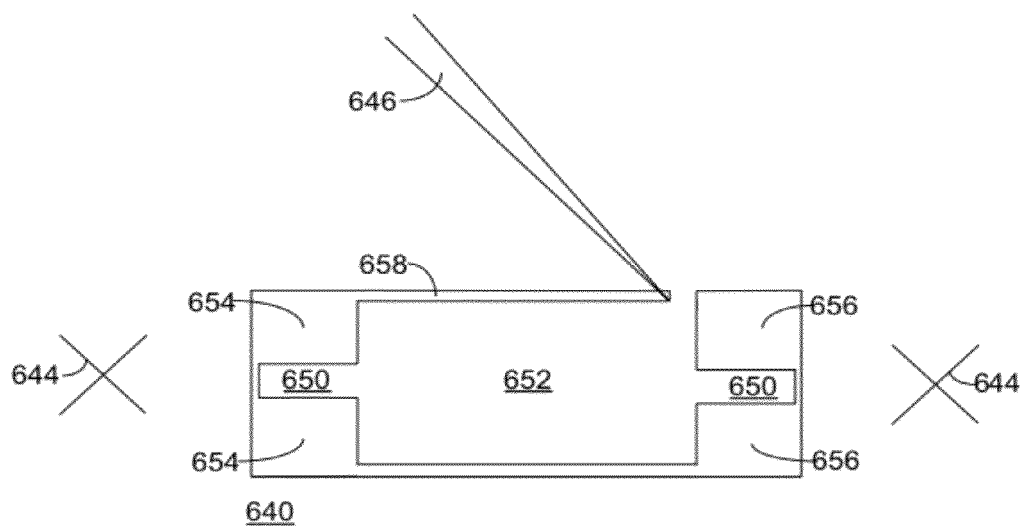
FIGS. 27-28 illustrate steps in separating a modified chunk-type sample from a substrate according to the present invention.

FIG. 27 shows an illustration of a sample according to a preferred embodiment of the present invention after two wings 650 have been formed. In a preferred embodiment, each wing will be formed by using a FIB to cut two adjacent rectangular cavities 654 and 656 at either end of the chunk-type center section 652, the remaining material between each set of two adjacent rectangles forming two thin sample sections having substantially vertical faces. The cavities formed by milling within the adjacent rectangles are preferably 5-8 μm deep and 5-8 μm wide. Preferably, the FIB will be substantially normal with respect to the sample surface when the rectangles are milled. A typical cross-section mill pattern can be used coming in from both sides of each wing, leaving a coarse wing approximately 2 μm thick. Optionally, in step 508, the wings can then be further thinned to approximately 100 nm with a cleaning cross-section mill on both sides. In a preferred embodiment, the final wing section will be approximately 100 nm thick×10-20 μm wide×5-8 μm deep.

In a preferred embodiment, one of the wings can be used as an attachment location for the probe tip for an automated sample extraction system as discussed above. The other wing can serve as a clamping location for attachment to a TEM sample holder. Depending on the method used to mount the sample onto a TEM sample holder, it may not be necessary to form the second TEM sample holder attachment wing. In some embodiments, the wing used for TEM sample holder attachment may be of a different shape and/or have different dimensions that the probe attachment wing. In other embodiments, the sample can essentially be formed as a much thicker lamella, for example 5 to 10 μm thick with no wings at all.

Figure 28:
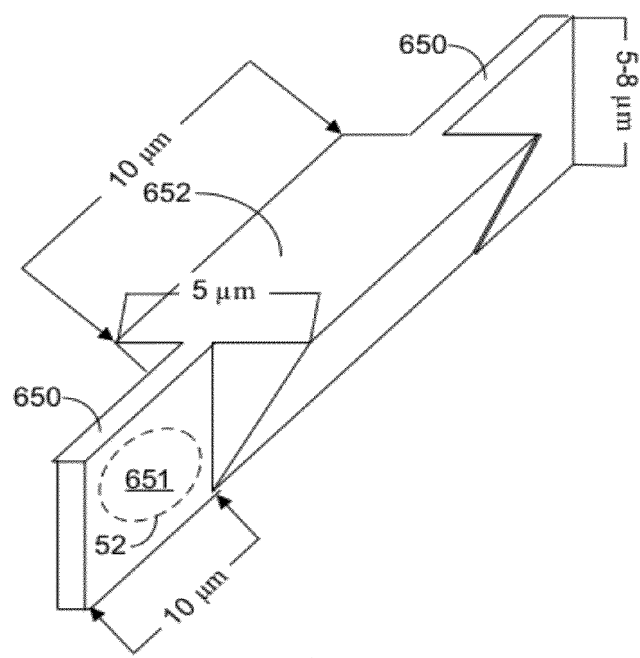

In step 510, the FIB is again tilted with respect to the sample surface (for example to approximately 45 degrees) and the sample is then rotated 180 degrees and a trench milled along the top of the initial U-shaped trench in order to finish freeing the sample. FIG. 27 shows a sample with the top trench 658 almost completely milled. FIG. 28 shows a preferred embodiment of a completed and extracted sample according to the present invention is having a center section 652 that is approximately 10 μm (length)×5 μm (width) and two wings 650 that are approximately 10 μm long×5-8 μm deep.

Because a high degree of precision is not required to mill the one or more sample wings (because the feature of interest is contained within the larger wedge-shaped center section) separating the sample can be rapidly accomplished, allowing the wafer to be more quickly returned to the production line. Forming the one or more wings requires only 5-10 additional minutes of FIB milling as compared to forming the purely wedge-shaped sample as in the prior art. As discussed below, the sample structure according to the present invention also helps preserve sample orientation when the sample is transferred to a TEM finger grid.

If there are any additional samples to be extracted (step 512), the FIB system can navigate to each additional sample site (step 514) and repeat the process described in steps 502 to 510. In step 516, once the milling has been completed at all desired sample locations, the wafer is transferred to a sample extraction tool, such as the ESP sample extraction tool described in greater detail above. Wafers (with all samples milled) are preferably transferred to the ESP by way of a multi-wafer carrier and auto-loading robot, as in well known in the art, although wafers can also be transferred manually.

Figure 9:
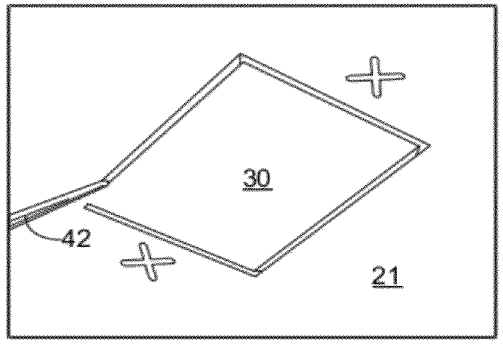
FIGS. 9-10 show steps in a typical in-situ lift out of a chunk-type TEM sample according to the prior art.
Figure 10:
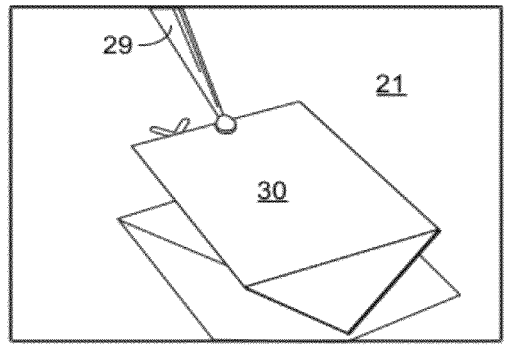
Figure 11:
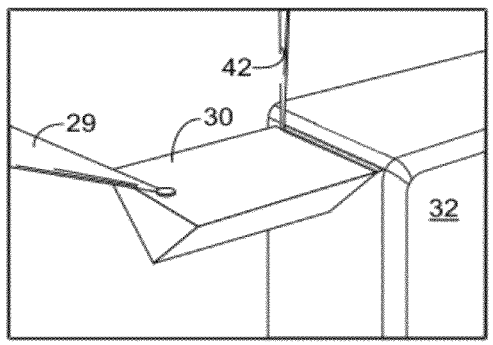
FIGS. 11-12 show the process of attaching the sample of FIGS. 10-13 to a TEM sample holder according to the prior art.
Figure 12:
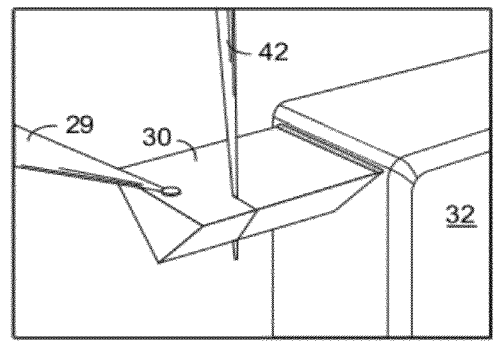
Figure 29:
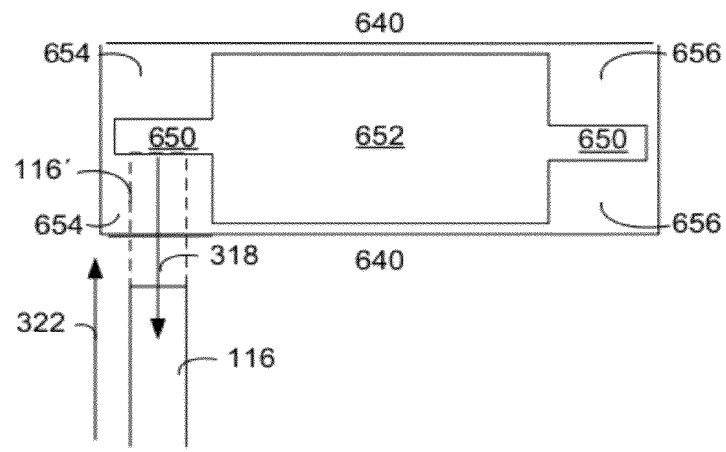
FIG. 29 shows a sample extracted from a substrate according to the present invention.
Figure 30:
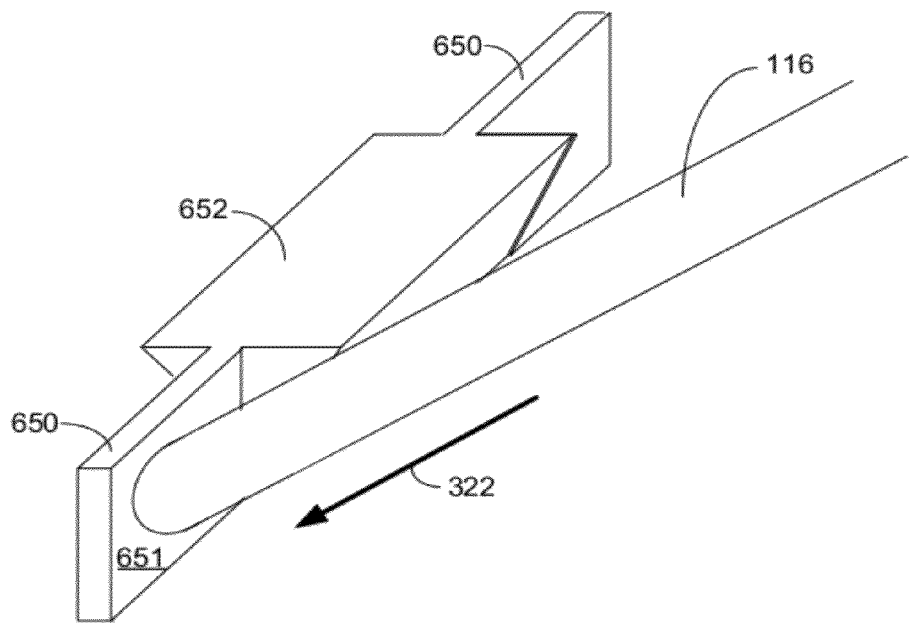
FIG. 30 shows a probe attached to the sample of FIG. 29.

In step 518, the ESP probe navigates to the sample to be extracted. The sample extraction tool preferably uses a mechanical stage to navigate to each sample site. In step 520, the probe 116 is attached to the vertical face 651 on one of the sample wings 650 as shown in FIG. 29 and FIG. 30, preferably by way of vacuum pressure as discussed above, and the probe is used to transfer the sample to a TEM sample holder such as a prior art TEM finger grid shown in FIG. 9. In some embodiments, the TEM sample holder is compatible with FEI's Ultraview™ sample transfer capsules. The sample extraction process is preferably fully automated. Alternatively, the extraction process can be completely or partially controlled manually. The sample holder can also be rotated in the appropriate direction to account for orientation errors in the positioning of the sample. The sample can be held in place on the TEM sample holder by any appropriate method, such as glue or adhesive, with the shape of the vertical wing serving to improve the security of attachment and to aid in maintaining the proper orientation of the sample.

Once the sample has been attached to the holder, the probe can be detached and moved back to the wafer to extract another sample. Once all samples have been extracted, in step 524 the wafer is returned to the production line. In step 526, the samples are transferred by way of the TEM sample holder to a second Dual Beam FIB for further thinning and analysis. After sample thinning is completed, in step 528, the sample can then be transferred to an S/TEM for imaging.

Figure 31:
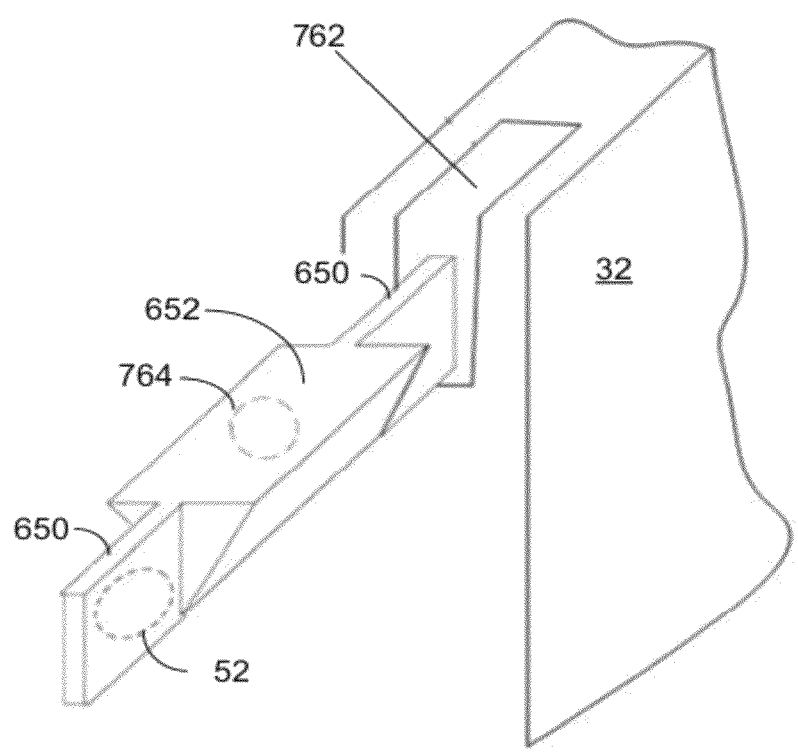
FIG. 31 shows a sample attached to a TEM sample holder according to a preferred embodiment of the present invention.

In one preferred embodiment, as shown in FIG. 31, a notch 762 can be formed on one or more of the fingers 32 on a TEM finger grid. The probe can be used to slide vertical wing 650 into the notch 762 where it can be held in place by friction (requiring a tight fit between the wing and notch) or by other means such as a UV curable adhesive or glue. In order to make it easier to position the sample and/or to prevent the probe from making contact with the finger grid as the sample is moved into position, in some embodiments the probe tip can attached on the top surface of the sample in the area indicated by dashed line 764. In order to attach probe tip to the horizontal surface of the sample, the probe can be rotated 180 degrees (around the cylindrical axis of the probe) so that the beveled tip is parallel to the top of the sample. The probe can then be lowered until the tip makes contact with the sample and the vacuum applied to hold the sample against the probe tip.

Figure 32:
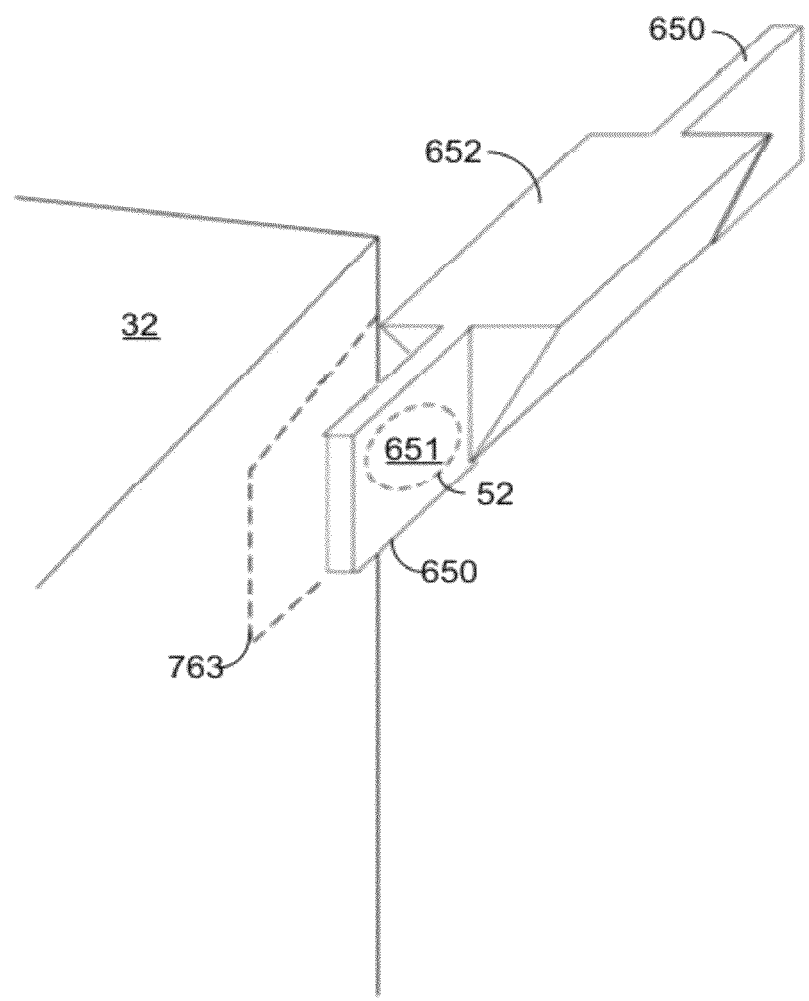
FIG. 32 shows a sample attached to a TEM sample holder according to a preferred embodiment of the present invention.

In the preferred embodiment shown in FIG. 32, the probe can be used to position the sample so that the vertical face of wing 650 is placed against the side of one of the fingers 32 on the TEM finger grid. A small amount of UV curable adhesive or glue can be applied to the finger sidewall in the area indicated by dashed line 763 using known methods and a UV light source used to cure the glue and hold the sample in place. In this embodiment, persons of ordinary skill in the art will recognize that the orientation of the sample can be precisely controlled because the vertical wing 650 is held firmly against the vertical sidewall of finger 32. In some embodiments, the orientation can be altered by varying the angle of the sidewall of wing 650 relative to the feature of interest.

The invention has broad applicability and can provide many benefits as described and shown in the examples above. The embodiments will vary greatly depending upon the specific application, and not every embodiment will provide all of the benefits and meet all of the objectives that are achievable by the invention. For example, in a preferred embodiment TEM samples are created using a gallium liquid metal ion source to produce a beam of gallium ions focused to a sub-micrometer spot. Such focused ion beam systems are commercially available, for example, from FEI Company, the assignee of the present application. However, even though much of the previous description is directed toward the use of FIB milling, the milling beam used to process the desired TEM samples could comprise, for example, an electron beam, a laser beam, or a focused or shaped ion beam, for example, from a liquid metal ion source or a plasma ion source, or any other charged particle beam. Also, the invention described above could be used with automatic defect reviewing (ADR) techniques, which could identify defects via die-to-die or cell-to-cell ADR. A sample containing the defect could be created and removed with or without milling fiducials. Further, although much of the previous description is directed at semiconductor wafers, the invention could be applied to any suitable substrate or surface. Also, although much of the previous description is directed at generally rectangular shaped lamellae which are less than 100 nm thick, the present invention could be used with lamellae of other thicknesses and with samples having other shapes. The accompanying drawings are intended to aid in understanding the present invention and, unless otherwise indicated, are not drawn to scale.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of extracting a lamella from a substrate comprising;
    placing the substrate with the lamella to be extracted on a moveable stage, the lamella being physically attached to the substrate;
    moving a microprobe into contact with the lamella, the microprobe comprising a hollow tube connected to a vacuum source and open at the microprobe tip;
    applying a vacuum through the microprobe tip so that the vacuum holds the sample against the microprobe tip;
    lifting the microprobe with attached sample away from the substrate, severing the attachment of the lamella to the substrate;
    moving the microprobe so that the sample is in contact with a desired position on a sample holder;
    moving the microprobe away from the released sample.

2. The method of claim 1 wherein moving the probe tip into contact with the lamella comprises moving the probe tip until it makes contact with the lamella and then moving the probe forward to push the sample and break any remaining connection between the lamella and the substrate.

3. The method of claim 1 wherein moving the microprobe so that the sample is in contact with a desired position on a sample holder comprises moving the microprobe so that the sample is in contact with a desired position on a sample holder and then turning off the vacuum through the microprobe tip so that the sample is released from the microprobe tip.

4. The method of claim 3 further comprising applying a positive pressure through the microprobe after the sample is placed at the desired position on the sample holder.

5. The method of claim 1 in which the lamella has a substantially vertical sample face and in which moving a microprobe into contact with the lamella comprises:
    positioning the substrate relative to a microprobe having a cylindrical axis so that the cylindrical axis lies in a plane which is perpendicular to the sample face, said microprobe connected to a micromanipulator and mounted onto a probe stage that can rotate about the cylindrical axis of the probe, said microprobe having a generally flat tip which is beveled at an oblique tip angle with respect to the cylindrical axis of the microprobe; and said microprobe oriented so that the cylindrical axis of the microprobe is at an oblique probe angle with respect to the sample face and so that the beveled probe tip is substantially parallel to the sample face; and
    moving the microprobe so that the flat tip of the probe tip is in contact with the sample face.

6. The method of claim 5 in which moving the probe so that the sample is in contact with a desired position on a sample holder comprises:
    rotating the probe around its cylindrical axis through a first rotational angle so that the face of the beveled probe tip and the sample face are substantially parallel to the surface of a sample holder;
    positioning the probe so that the sample is generally above a desired position on the sample holder; and
    lowering the probe until the sample comes in contact with the surface of the sample holder.

7. The method of claim 5 in which the probe angle is 45 degrees, the tip angle is 45 degrees, and the first rotational angle is 180 degrees.

8. The method of claim 1 in which extracting the sample does not take place inside an ion beam system.

9. The method of claim 1 further comprising, after placing the substrate with the lamella to be extracted on a moveable stage, moving the stage so that the approximate x-y coordinates of a lamella to be extracted are within the field of view of an optical microscope;
    directing a light source at the lamella at an acute angle relative to the substrate surface;
    rotating the stage so that the illumination from the light source is directed in a plane perpendicular to the vertical face of the lamella; and
    using computer-based image recognition software to identify the precise location of the lamella.

10. A method for extracting a sample from a substrate, the method comprising:

mounting the substrate with the sample to be extracted on a moveable stage, the sample having a planar face to be used as a probe attachment site;

positioning the substrate relative to a microprobe having a cylindrical axis so that the cylindrical axis lies in a plane which is perpendicular to the sample face, said microprobe connected to a micromanipulator and mounted onto a probe stage that can rotate about the cylindrical axis of the probe, said microprobe having a generally flat tip which is beveled at an oblique tip angle with respect to the cylindrical axis of the microprobe; and said microprobe oriented so that the cylindrical axis of the microprobe is at an oblique probe angle with respect to the substrate surface and so that the beveled probe tip is substantially parallel to the sample face;

moving the microprobe so that the microprobe tip comes into contact with a vertical face on the sample, the sample being physically connected to the substrate;

lifting the microprobe with attached sample away from the substrate, severing the connection between the sample and the substrate;

rotating the probe around its cylindrical axis through a first rotational angle so that the face of the beveled probe tip and the sample face are substantially parallel to the surface of a sample holder;

positioning the probe so that the sample is generally above a desired position on the sample holder;

lowering the probe until the sample comes in contact with the sample holder;

depositing the sample onto the sample holder;

moving the probe away from the released sample.

11. The method of claim 10 wherein said planar face is at a first sample angle relative to the substrate surface and wherein the combination of the tip angle and the probe angle equal the angle of the planar face.

12. The method of claim 10 further comprising applying a vacuum to the microprobe through an open microprobe tip so that the vacuum holds the sample against the microprobe tip.

13. The method of claim 10 further comprising, after placing the substrate with the sample to be extracted on a moveable stage, moving the stage so that the approximate x-y coordinates of the sample to be extracted are within the field of view of an optical microscope;

directing a light source at the sample at an acute angle relative to the substrate surface;

rotating the stage so that the illumination from the light source is directed in a plane perpendicular to the planar face of the sample; and using computer-based image recognition software to identify the precise location of the sample.

14. The method of claim 1 in which severing the attachment between the sample and the substrate does not take place inside an ion beam system.

15. The method of claim 1 further comprising determining if a lamella is present using a light source positioned at an oblique angle with respect to the substrate surface to illuminate the lamella.

* * * * *

UNITED STATES PATENT AND TRADEMARK OFFICE
CERTIFICATE OF CORRECTION

PATENT NO. : 8,357,913 B2
APPLICATION NO. : 12/446376
DATED : January 22, 2013
INVENTOR(S) : Enrique Agorio et al.

It is certified that error appears in the above-identified patent and that said Letters Patent is hereby corrected as shown below:

In the Claims:

Column 16, Line 49, Claim 7 – Please change "claim 5" to read --claim 6--.

Signed and Sealed this
Thirtieth Day of July, 2013

Teresa Stanek Rea
*Acting Director of the United States Patent and Trademark Office*